United States Patent
Iqbal et al.

(10) Patent No.: US 10,323,082 B2
(45) Date of Patent: Jun. 18, 2019

(54) TREATMENT OF TAUOPATHIES BY PASSIVE IMMUNIZATION TARGETING THE N-TERMINAL PROJECTION DOMAIN OF TAU

(71) Applicant: The Research Foundation for Mental Hygiene, Inc., Menands, NY (US)

(72) Inventors: Khalid Iqbal, Staten Island, NY (US); Inge Grundke-Iqbal, Staten Island, NY (US)

(73) Assignee: THE RESEARCH FOUNDATION FOR MENTAL HYGIENE, INC., Menands, NY (US)

( * ) Notice: Subject to any disclaimer, the term of this patent is extended or adjusted under 35 U.S.C. 154(b) by 0 days.

(21) Appl. No.: 14/880,425

(22) Filed: Oct. 12, 2015

(65) Prior Publication Data

US 2016/0102138 A1 Apr. 14, 2016

Related U.S. Application Data

(60) Provisional application No. 62/063,797, filed on Oct. 14, 2014.

(51) Int. Cl.
*A61K 39/00* (2006.01)
*C07K 16/18* (2006.01)

(52) U.S. Cl.
CPC ........ *C07K 16/18* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS

2014/0234214 A1* 8/2014 Griswold-Prenner ...................... C07K 16/18
424/1.49

OTHER PUBLICATIONS

Chen "Enhancement and destruction of antibody function by somatic mutation: unequal occurrence is controlled by V gene combinatorial associations" EMBO Journal vol. 14 No. 1 2 pp. 2784-2794 (Year: 1995).*
Kussie "A Single Engineered Amino Acid Substitution Changes Antibody Fine Specificity" J immunol 152(1):146-52 (Year: 1994)*
Biolegend "Purified anti tau 1-100 antibody" accessed from biolegend. com on Nov. 2, 2018 (Year: 2018).*
Liu "site-specific effects of tau phosphorylation on its microtubule assembly activity and self-aggregation" eur j neurosci 26(12):3429-3436 (Year: 2007).*

* cited by examiner

*Primary Examiner* — Adam Weidner
(74) *Attorney, Agent, or Firm* — Bond Schoeneck & King, PLLC; David Nocilly

(57) ABSTRACT

A method of treating tau pathologies, such as Alzheimer's disease, involving the administration of antibodies specific to the amino terminal region of human tau (amino acid residues 6-18 or 184-195) to provide passive immunization. The administration of such antibodies can reduce total tau levels, decrease tau hyperphosphorylation, and improve reference memory. Passive immunization with antibodies targeting the N-terminal projection domain of tau reduces both total and hyperphosphorylated tau was found effective in aged 3×Tg-AD mice, a generally accepted mouse model of Alzheimer's disease and frontotemporal dementia in humans.

3 Claims, 25 Drawing Sheets

Figures 1A, 1B:
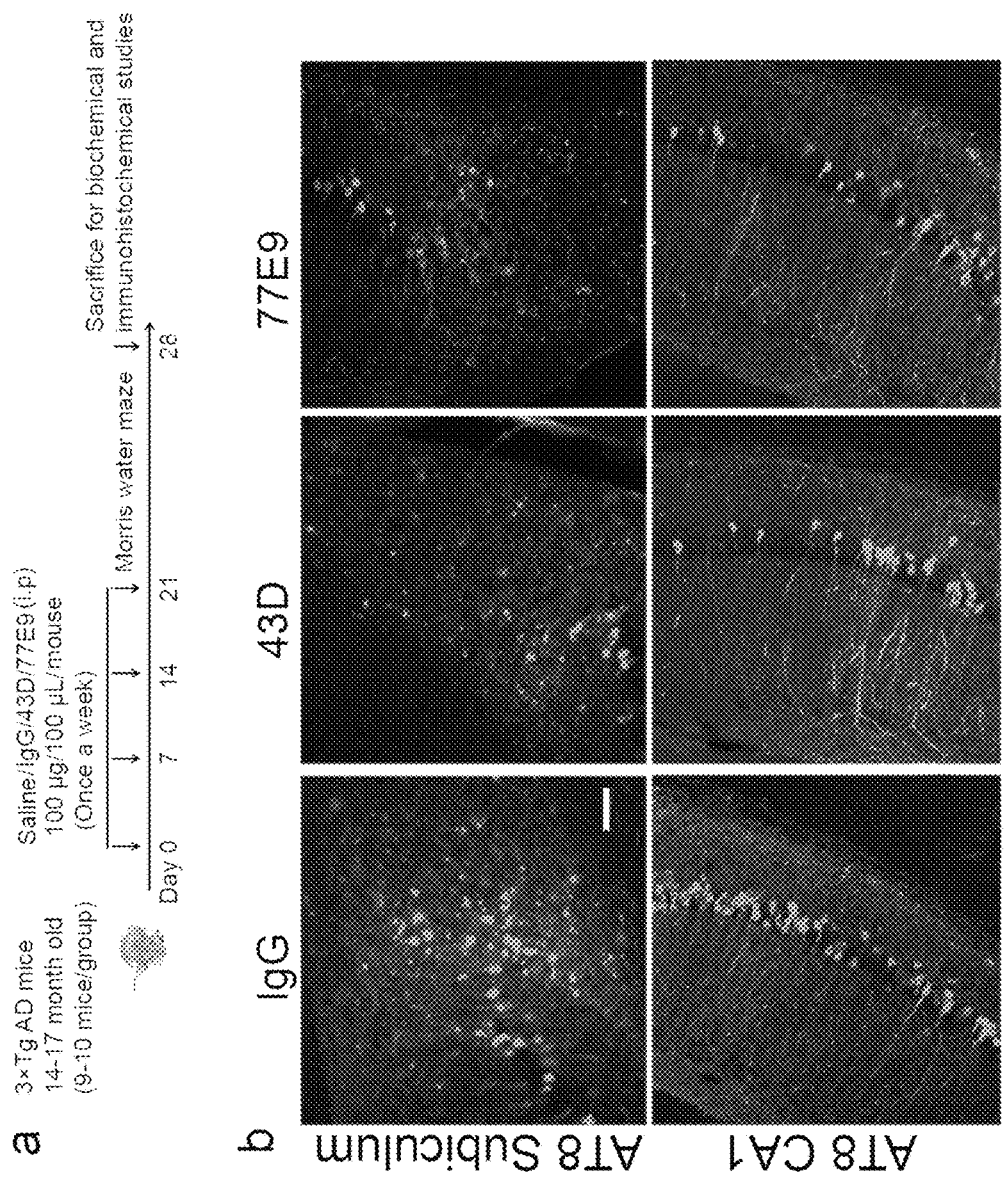

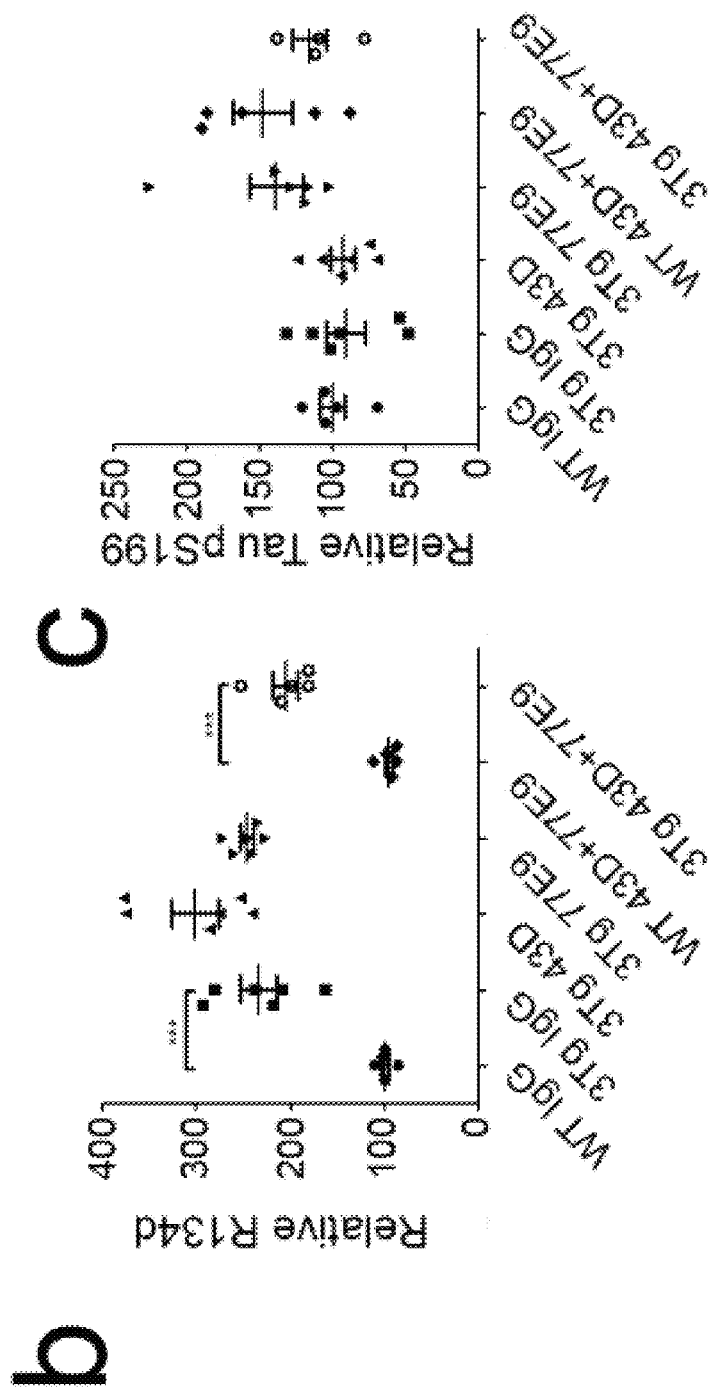
Fig. 11(b) through (c)

TREATMENT OF TAUOPATHIES BY PASSIVE IMMUNIZATION TARGETING THE N-TERMINAL PROJECTION DOMAIN OF TAU

BACKGROUND OF THE INVENTION

1. Field of the Invention

The present invention relates to the treatment of taupathies and, more particularly, to passive immunization targeting the N-terminal projection domain of tau.

2. Description of the Related Art

Alzheimer's disease (AD) is the most common type of dementia and is characterized by progressive loss of memory and other cognitive functions. The two major histopathological hallmarks in brains of AD patients are extracellular senile plaques consisting of amyloid-β (Aβ) peptides and intracellular neurofibrillary tangles (NFTs), composed of abnormally hyperphosphorylated tau protein. The tau pathology made up of the hyperphosphorylated tau is also a hallmark of several neurodegenerative disorders, which include frontolobar dementias, the corticobasal degeneration, progressive supranuclear palsy, Pick disease, Guam Parkinsonism dementia complex, and dementia pugilistica. The density of tau lesions directly correlates with dementia.

At present, there is no effective treatment available for AD and related tauopathies. Most therapeutic approaches for AD mainly focused on reducing Aβ levels in the brain which included blocking the formation of Aβ by modulating β-secretase and/or γ-secretase, promoting the clearance of Aβ, preventing aggregation of Aβ and destabilizing Aβ oligomers; however, to date, none of these approaches have yielded a successful outcome. The first tau immunotherapy targeting active immunization against truncated tau, tau 151-391, is now in Phase I human clinical trial.

Harnessing the immune system to prevent or remove the Aβ and tau aggregates is an emerging and promising disease-modifying approach for AD. In the last decade, Aβ immunotherapy progressed from preclinical studies in transgenic mouse models of AD to clinical trials in humans. While immunization with Aβ increased the clearance of Aβ, it failed to reduce neurofibrillary pathology and prevent progressive neurodegeneration. Furthermore, Aβ immunotherapies showed little cognitive benefit in mild-to-moderate AD patients. Importantly, multivariate analyses indicate that neurofibrillary tangles, neuron number loss and synapse loss, but not amyloid load, strongly correlate with cognitive impairment in AD patients. These findings have led to the belief that targeting tau pathology might be more effective than Aβ-directed therapy for AD.

Intracellular aggregates of tau locate inside of neuron, which complicates its targeting for clearance. However, active immunization with recombinant α-synuclein in a transgenic mouse model was found to decrease aggregates of α-synuclein, an intracellular synaptic protein that accumulates in the brains of patients with Parkinson's disease and AD. This finding supported that intracellular proteins could also be potential targets for immunotherapy. Indeed, immunotherapy targeting pathological tau has been tested in several AD transgenic mouse models with different phospho-tau peptides. Accumulating evidence from these preclinical studies has shown that active immunization in transgenic tauopathy mouse models using tau phosphopeptides reduce tau pathology and rescue or slow the cognitive decline. Passive immunotherapy using antibodies against pathology of tau has also been shown to slow disease progression.

Tau pathology is believed to spread transcellularly. The abnormally hyperphosphorylated/oligomeric tau released in the extracellular space from the affected neurons is suspected to serve as the seeds for the spread of tau pathology by the ingesting cells. Therefore, tau immunotherapy may clear extracellular tau that is involved in the spreading of tau pathology. One study screened tau antibodies with the ability to block seeding activity present in P301S brain; infusion of tau antibodies specific for blocking P301S tau seeds into the lateral ventricle of P301S mice for 3 months reduced hyperphosphorylated, aggregated and insoluble tau, blocked development of tau seeding activity, and improved cognitive deficits. This finding indicated that tau immunotherapy can target its transcellular propagation.

Tau protein consists of an N-terminal projection region, a proline-rich domain, a microtubule-binding domain, and a C-terminal region. Although the role of tau in regulating microtubule dynamics is extensively established, much less is known about the functional role of the N-terminal domain of tau on neuron survival. A 17-kD N-terminal tau fragment generated by calpain cleavage, comprising residues amino acid 45-230, was proposed to mediate Aβ-induced toxicity, and mediate tau neurotoxicity in Drosophila tauopathy model. However, the toxicity and in vivo relevance of this 17 kD fragment are debated. Garg et al. reported that this 17 kD fragment cleaved by calpain is tau 125-230, which is much shorter than previously reported tau 45-230. Furthermore, both tau 125-230 and tau 45-230 fragments showed no toxicity in Chinese hamster ovary (CHO) cells, neuroblastoma cells (N2a) and in primary hippocampal neurons. Other N-terminal tau fragments including tau 1-44, tau 26-44, tau 26-230 and tau 1-156 were reported to cause an NMDAR-mediated powerful toxicity in cerebellar granule neurons, but tau 45-230 exerted a toxicity with unknown mechanism. Tau 1-230 was also reported to protect neuron from apoptosis, which indicated that N-terminal domain of tau can be either neuroprotective or neurotoxic according to its length. Alzheimer abnormally hyperphosphorylated tau, instead of interacting with tubulin and promoting its assembly into microtubules, sequesters normal tau, forming oligomers and consequently filaments which can be sedimented at 100,000 to 200,000×g.

BRIEF SUMMARY OF THE INVENTION

The present invention comprises passive immunization with tau antibodies for the treatment of tauopathies. In a first example, 14-17-months-old 3×Tg-AD mice were treated with tau antibodies 43D (tau 6-18) and 77E9 (tau 184-195) to the N-terminal projection domain of tau or mouse IgG as a control by intraperitoneal injection once a week for four weeks, and the effects of the passive immunization on reduction of hyperphosphorylated tau, Aβ accumulation and cognitive performance in these animals. Treatment with tau antibodies 43D and 77E9 reduced total tau level, decreased tau hyperphosphorylated at Ser199, Ser202/Thr205 (AT8), Thr205, Ser262/356 (12E8) and Ser396/404 (PHF-1) sites, and a trend to reduce Aβ pathology. Most importantly, targeting N-terminal tau especially by 43D (tau 6-18) improved reference memory in the Morris water maze task in 3×Tg-AD mice. No abnormality was observed in the general physical characteristics of the treated animals with either of the two antibodies during the course of this study.

In a second example, 12-month-old 3×Tg-AD mice that represent a mild to moderate stage of the disease were immunized, two or six doses, i.v, once a week, of 15 μg of mouse control IgG, 43D, 77E9, or with a combination of 43D and 77E9. The dose-dependent effect of passive immunization with 43D and 77E9 antibodies on tau pathology and cognitive function in these animals were then analyzed. Same age of WT mice treated with mouse IgG or mixture of 43D and 77E9 were also used as controls. Two doses of tau antibodies 43D and 77E9 reduced total tau level, but had no significant impact on the levels of hyperphosphorylated tau. However, six treatments with tau antibody 43D reduced total tau level, and decreased hyperphosphorylated tau at Ser262/356 (12E8) and Ser396/404 (PHF-1) sites in hippocampus. Importantly, both 43D and 77E9 antibodies improved spatial memory in the Morris water maze in probe trial, though 3×Tg-AD mice immunized with 43D antibody but not 77E9 antibody took shorter time to find the hidden platform in the acquisition phase than that treated with mouse IgG in 3×Tg-AD mice. Furthermore, immunization with 43D and 77E9 antibodies rescued short memory impairment in 3×Tg-AD mice tested with one-trial novel object recognition test. The beneficial effect of passive immunization with 43D and 77E9 antibodies on short memory improvement could sustain even four months after discontinuing immunization as assessed by novel object location task. Additionally, six immunizations with 43D and 77E9 antibodies showed a trend to reduce Aβ pathology one month after the last immunization in the forebrain. No abnormality was observed in the general physical characteristics of animals treated with 43D, 77E9 or both antibodies combined during the course of this study.

These results indicate that: (1) passive immunization targeting normal tau can effectively clear the hyperphosphorylated protein and possibly reduce Aβ pathology from the brain; (2) targeting N-terminal projection domain of tau containing amino acid 6-18 is especially beneficial; and (3) passive immunization targeting normal N-terminal projection tau 6-18 and tau 184-195 dose-dependently can reduce total tau and decrease hyperphosphorylated tau in the brain, and can rescue cognitive deficits in 3×Tg-AD mice. Thus, passive immunization targeting selective epitopes of N-terminal domain of tau, such as tau 6-18 and tau 184-195, presents an effective therapeutic opportunity for Alzheimer disease and other tauopathies.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1(a) is a schematic showing the design of study where antibodies and, as control, mouse IgG or saline were administered intraperitoneally. The saline injected control group was used for behavioral studies, and IgG injected control animals were used for immunohistochemical and biochemical analysis FIG. 1(b) are images showing immunostaining of subiculum (SC) and CA1 from aged 3×Tg-AD mice immunized with 43D, 77E9 or control IgG using AT8 antibody and showing that passive immunization targeting the N-terminal projection domain of tau with 43D and 77E9 antibodies decreases tau hyperphosphorylation at Ser202/Thr205.

Figures 1C, 1D:
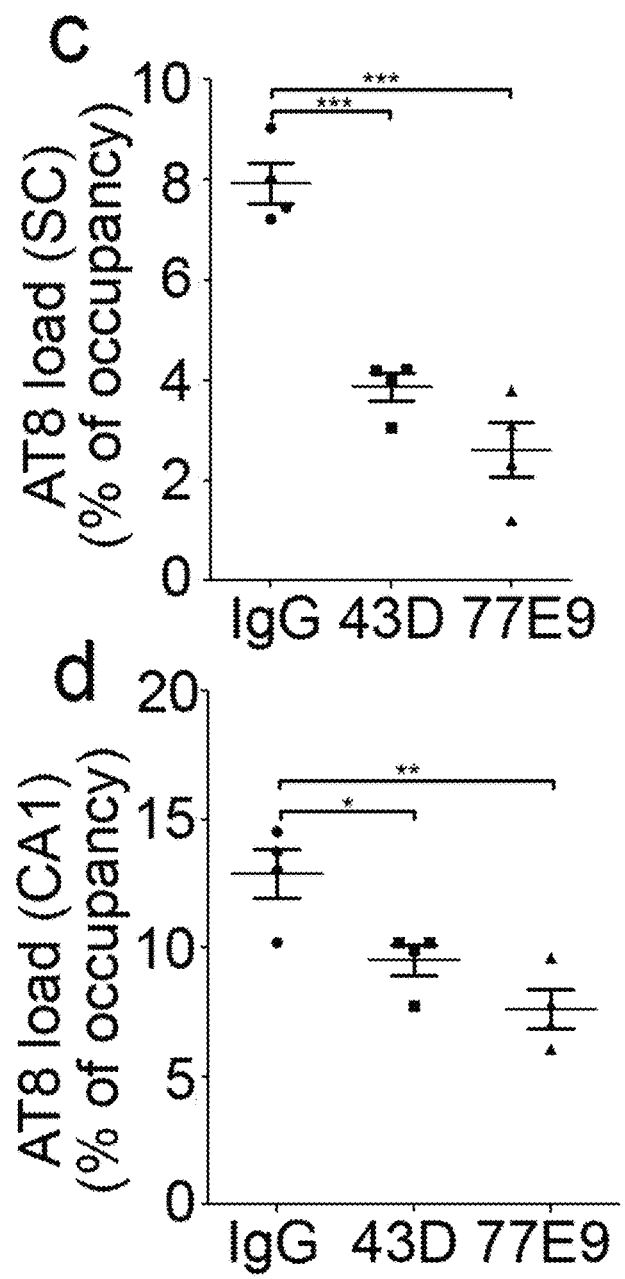

FIG. 1(c) is a scatter plot showing the quantification of AT8 immunostaining load in total subiculum from 3-4 serial sections from 4 mice per group. Scale bar=100 μm; data are shown as percentage of mouse IgG-treated animals (100%), mean±SEM; *$p<0.05$, $p<0.01$, *$p<0.001$ by unpaired two-tailed t-test.

Figure 2A:
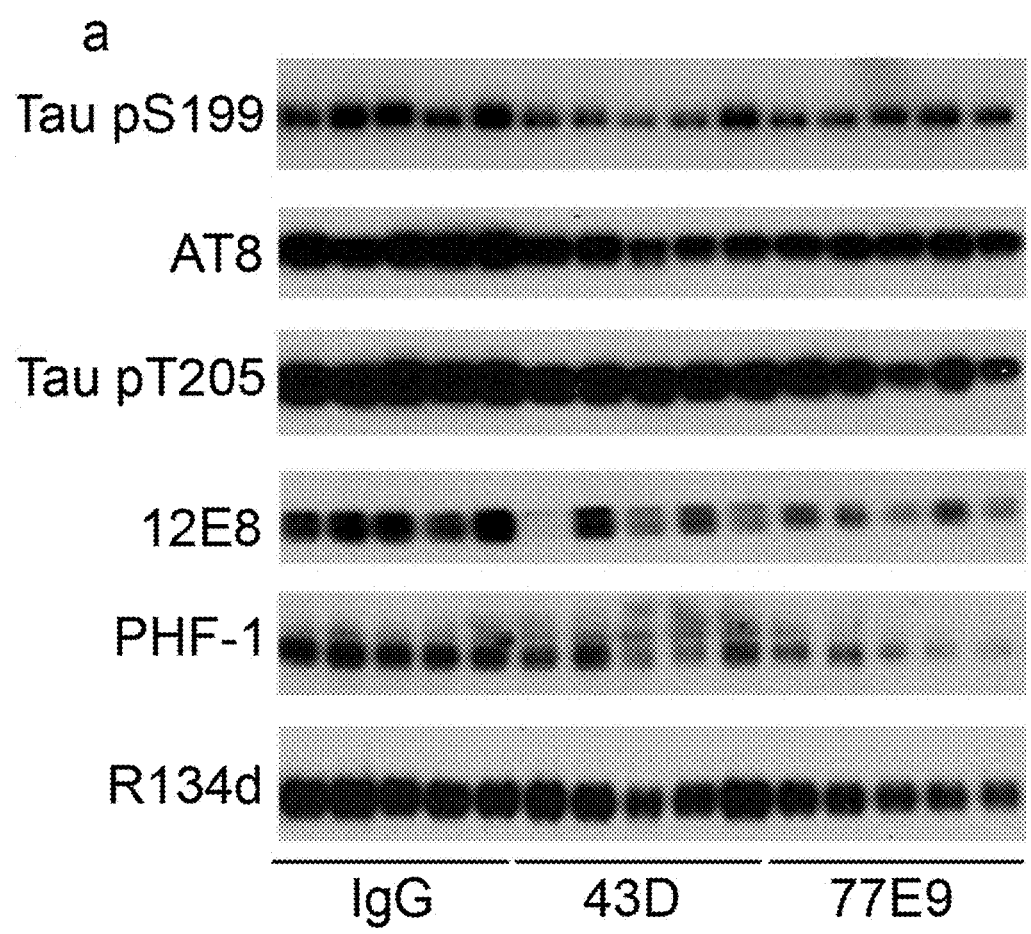
Figures 2B, 2C, 2D, 2E, 2F, 2G:
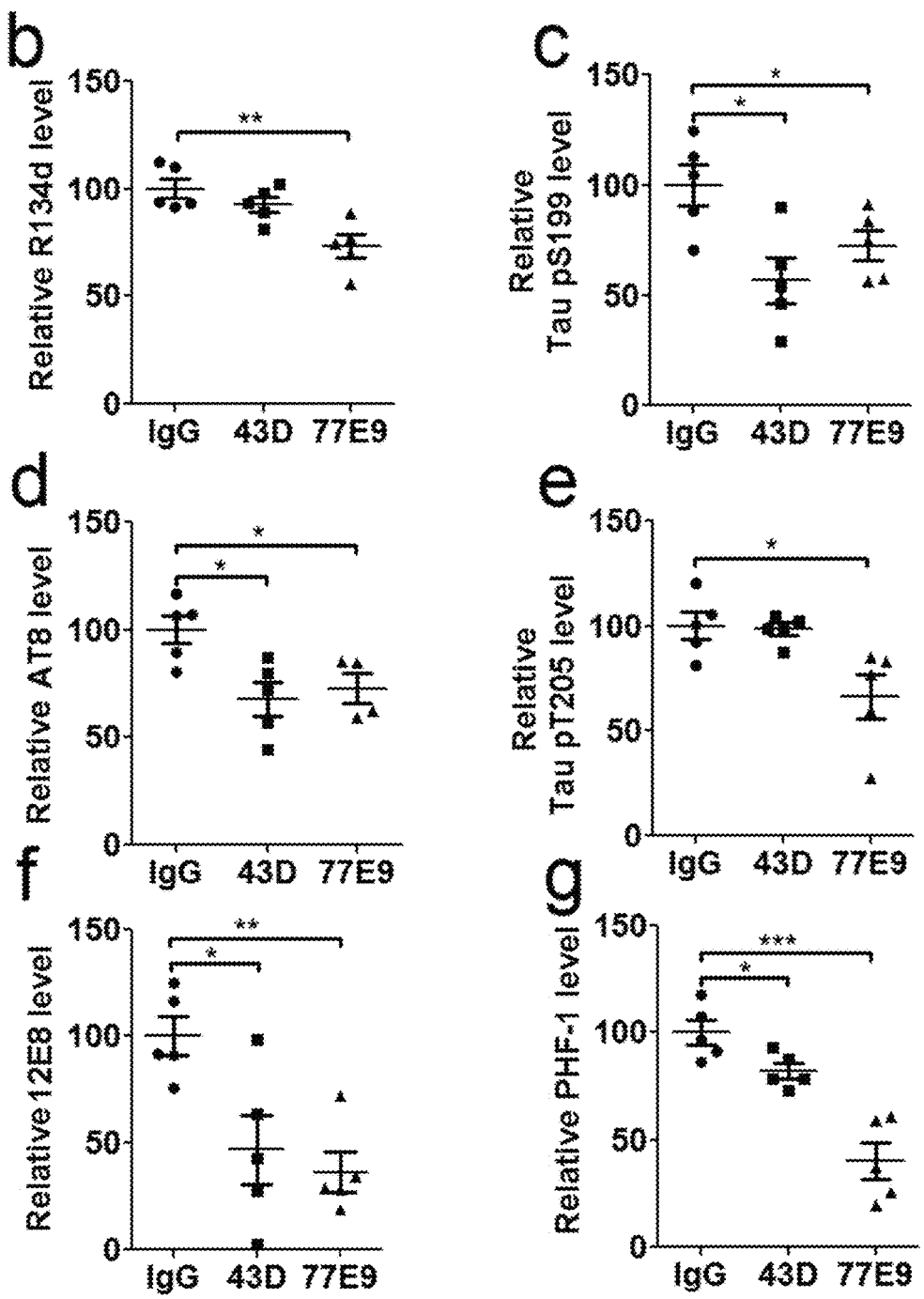

FIG. 1(d) is a scatter plot showing the quantification of AT8 immunostaining load in CA1 region from 3-4 serial sections from 4 mice per group. Scale bar=100 μm; data are shown as percentage of mouse IgG-treated animals (100%), mean±SEM; *$p<0.05$, $p<0.01$, *$p<0.001$ by unpaired two-tailed t-test FIG. 2(a) is a series of representative Western blots of hippocampus developed with R134d against total tau and several phosphorylation-dependent and site-specific tau antibodies showing that passive immunization targeting the N-terminal projection domain of tau with 43D and 77E9 antibodies reduces levels of total and hyperphosphorylated taus in hippocampus of aged 3×Tg-AD mice.

FIG. 2(b) through 2(g) are graphs showing densitometrical quantification of the blots after normalized with the GAPDH levels. Data are percentage of mouse IgG (100%)-treated animals reported as mean±SEM. *$p<0.05$,$p<0.01$, *$p<0.001$ by unpaired two-tailed t-test.

Figure 3A:
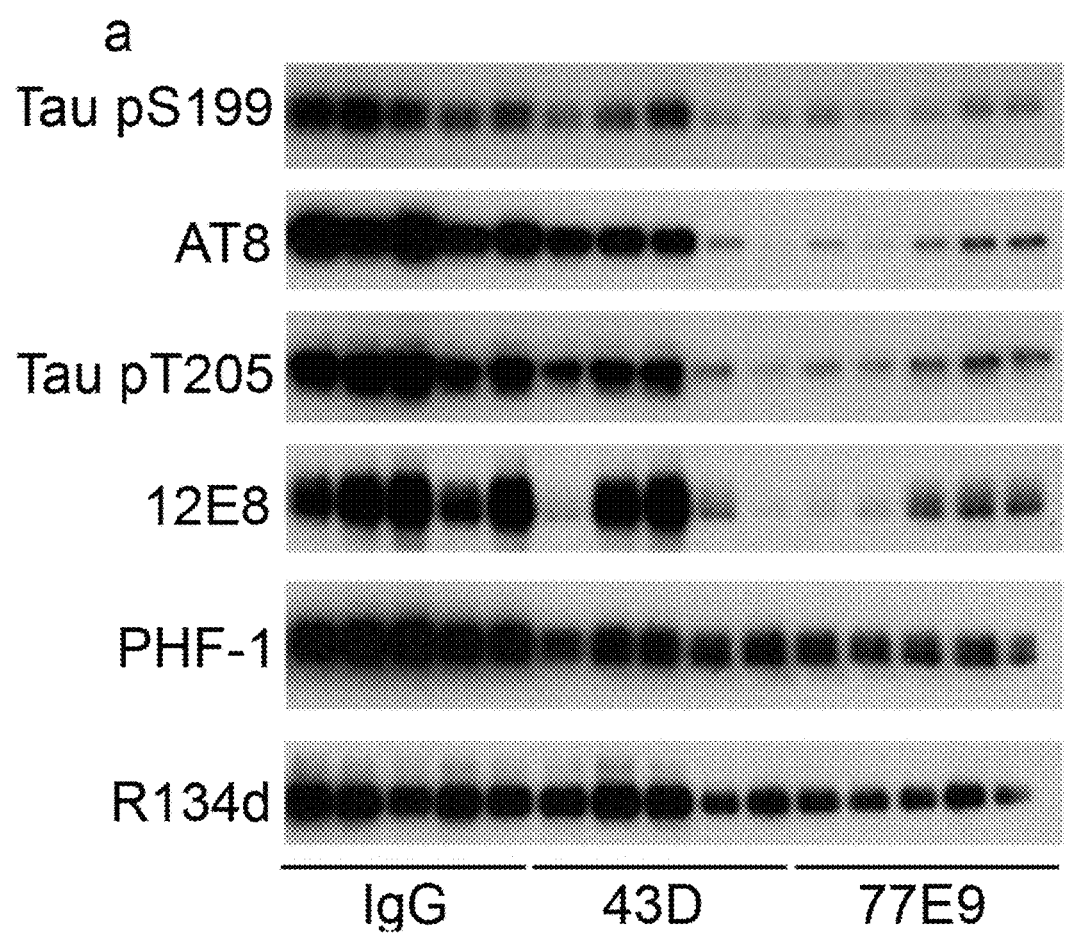
Figures 3B, 3C, 3D, 3E, 3F, 3G:
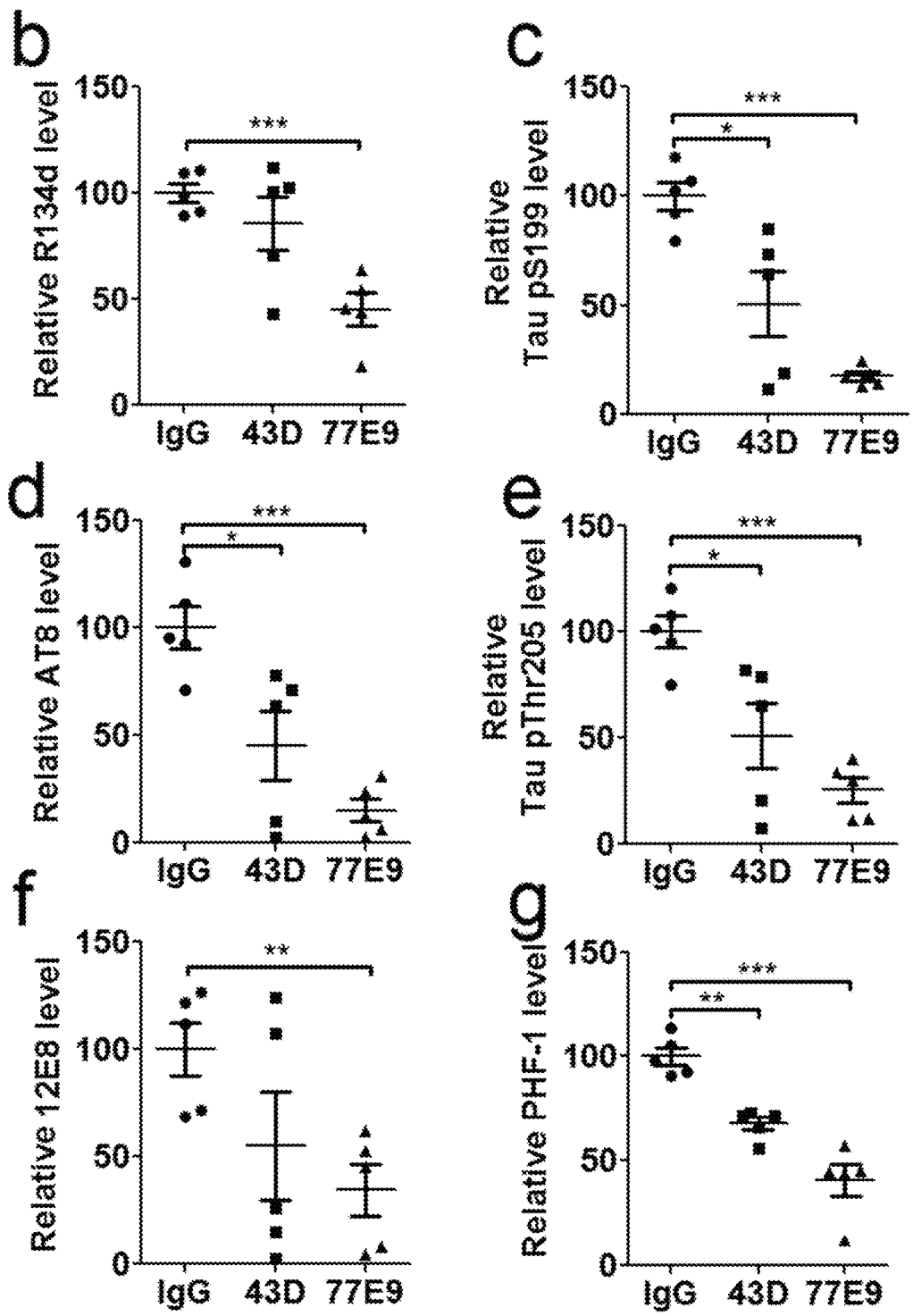

FIG. 3(a) is a series of representative Western blots of forebrain cortex developed with R134d against total tau and several phosphorylation-dependent and site-specific tau antibodies showing that passive immunization targeting the N-terminal projection domain of tau with 43D and 77E9 antibodies decreases levels of total and hyperphosphorylated taus in forebrain cortex of aged 3×Tg-AD mice.

FIGS. 3(b) through 3(g) are graphs showing densitometrical quantification of the blots after normalized with the GAPDH levels. Data are reported as mean±SEM.*$p<0.05$, $p<0.01$,*$p<0.001$ by unpaired two-tailed t-test.

Figures 4A, 4B, 4C, 4D:
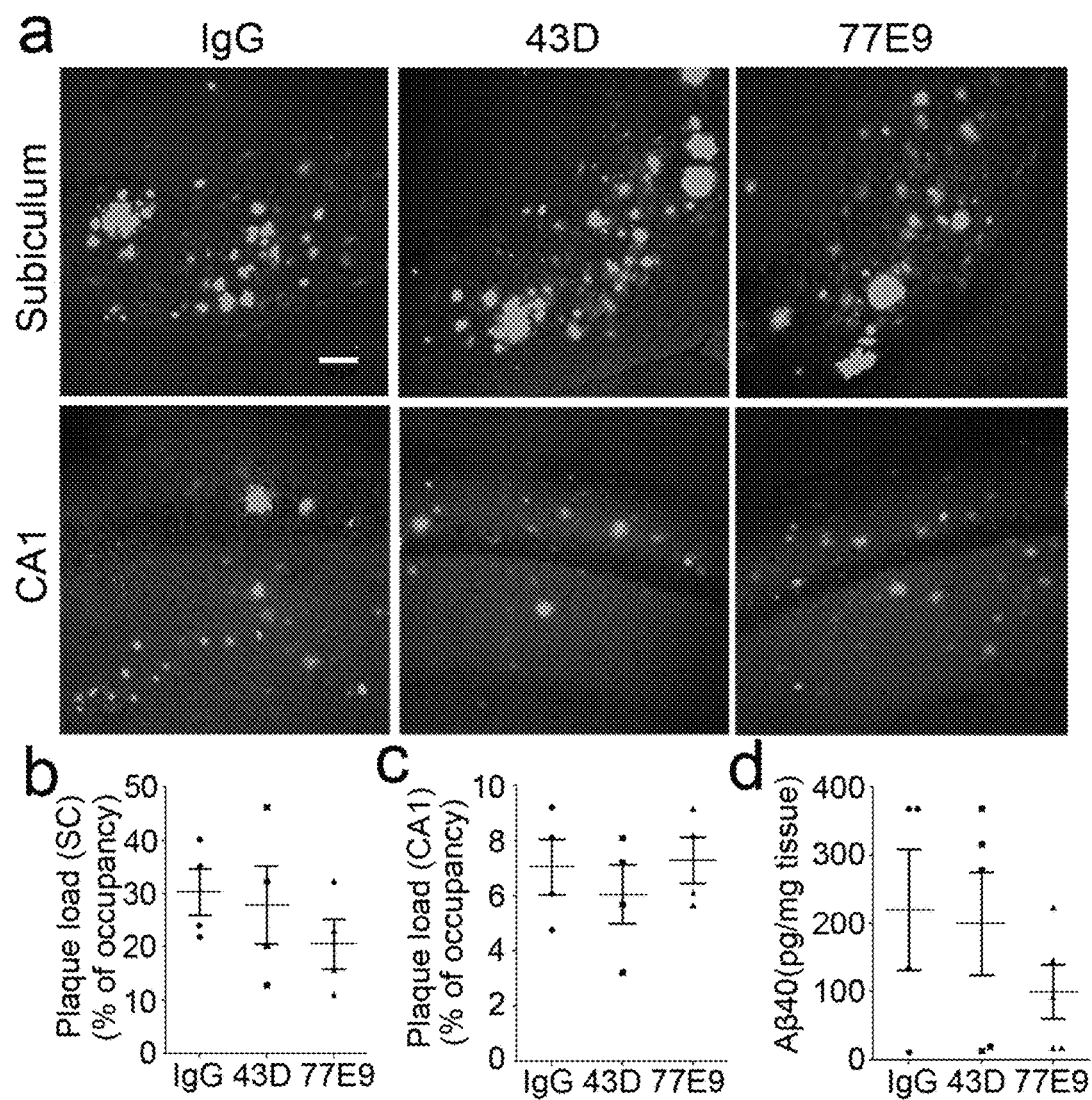

FIG. 4(a) is a series of images of immunostaining of subiculum (SC) and CA1 from aged 3×Tg-AD mice immunized with 43D, 77E9 and control IgG using Thioflavin-S showing that passive immunization targeting the N-terminal projection domain of tau with 43D and 77E9 antibodies show non-significant reduction of Thioflavin-S positive (TS+) amyloid plaques and level of Aβ40. Representative pictures of TS+ staining from subiculum (SC) and CA1 area. Scale bar=100 μm FIGS. 4(b) through 4(d) are scatter plots of the quantification of plaque load in total subiculum and CA1 region from 5-7 serial sections from 4 mice per group. The level of Aβ40 was quantified by ELISA and the data are shown as mean±SEM. Data was analyzed by unpaired two-tailed t-test.

Figures 5A, 5B, 5C, 5D, 5E:
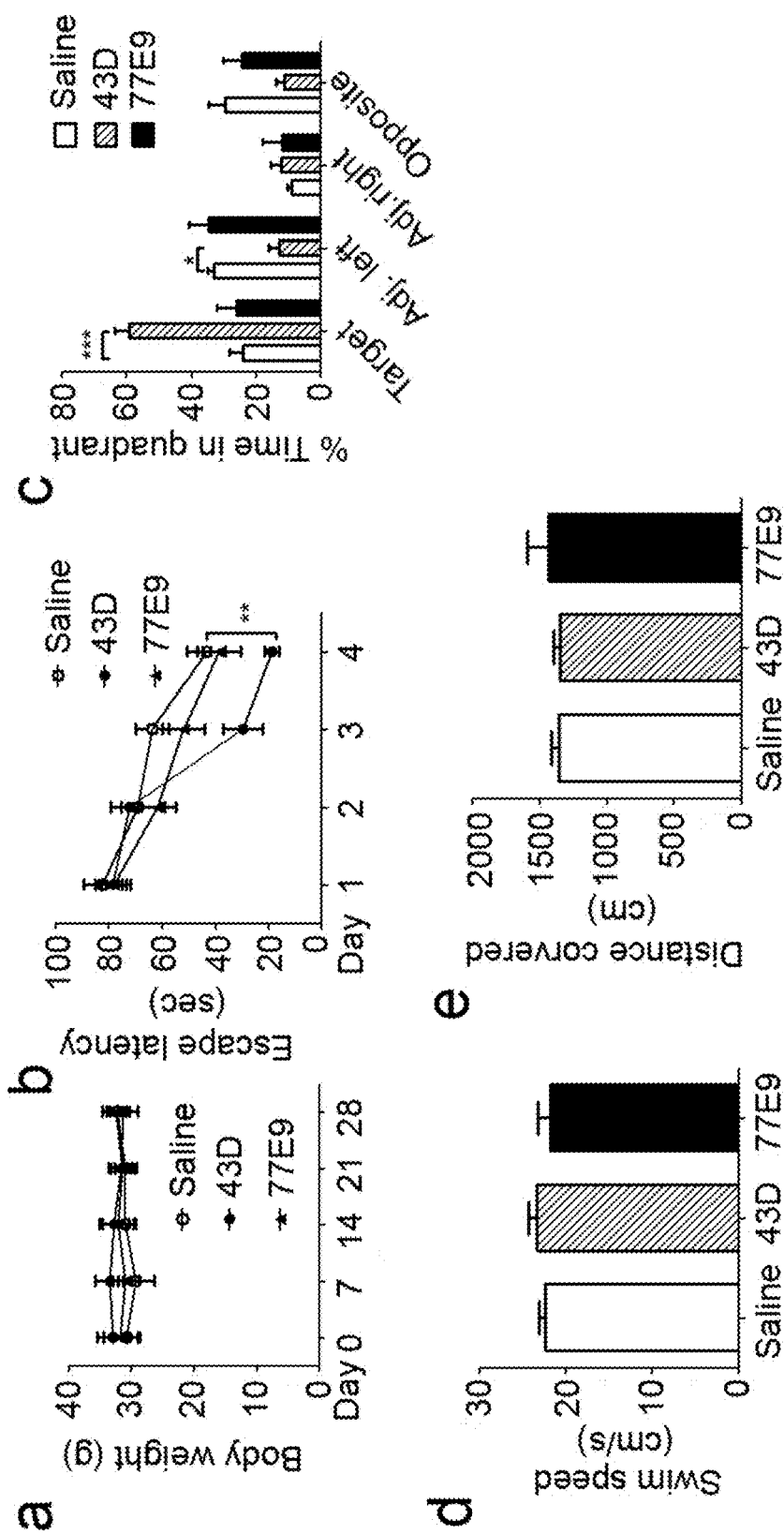

FIGS. 5(a) through 5(b) are a series of graph showing that passive immunization with tau antibody 43D improves cognitive performance without any side effects in aged 3×Tg-AD mice, where FIG. 5(a) shows the effect of the passive immunization on body weight and FIGS. 5(b) through 5(e) refer to reference memory in Morris water maze task where the body weights of the mice were measured once a week, the escape latency (sec) to reach the hidden platform was measured during acquisition phase for 4 days, the percent time in the quadrant during the probe trial was measured, and the average swim speed during the water maze training was determined. Data are reported as mean±SEM. *$p<0.05$,$p<0.01$,*$p<0.001$ vs. control mice by two-way ANOVA followed by a Bonferroni's posthoc test.

Figure 6A:
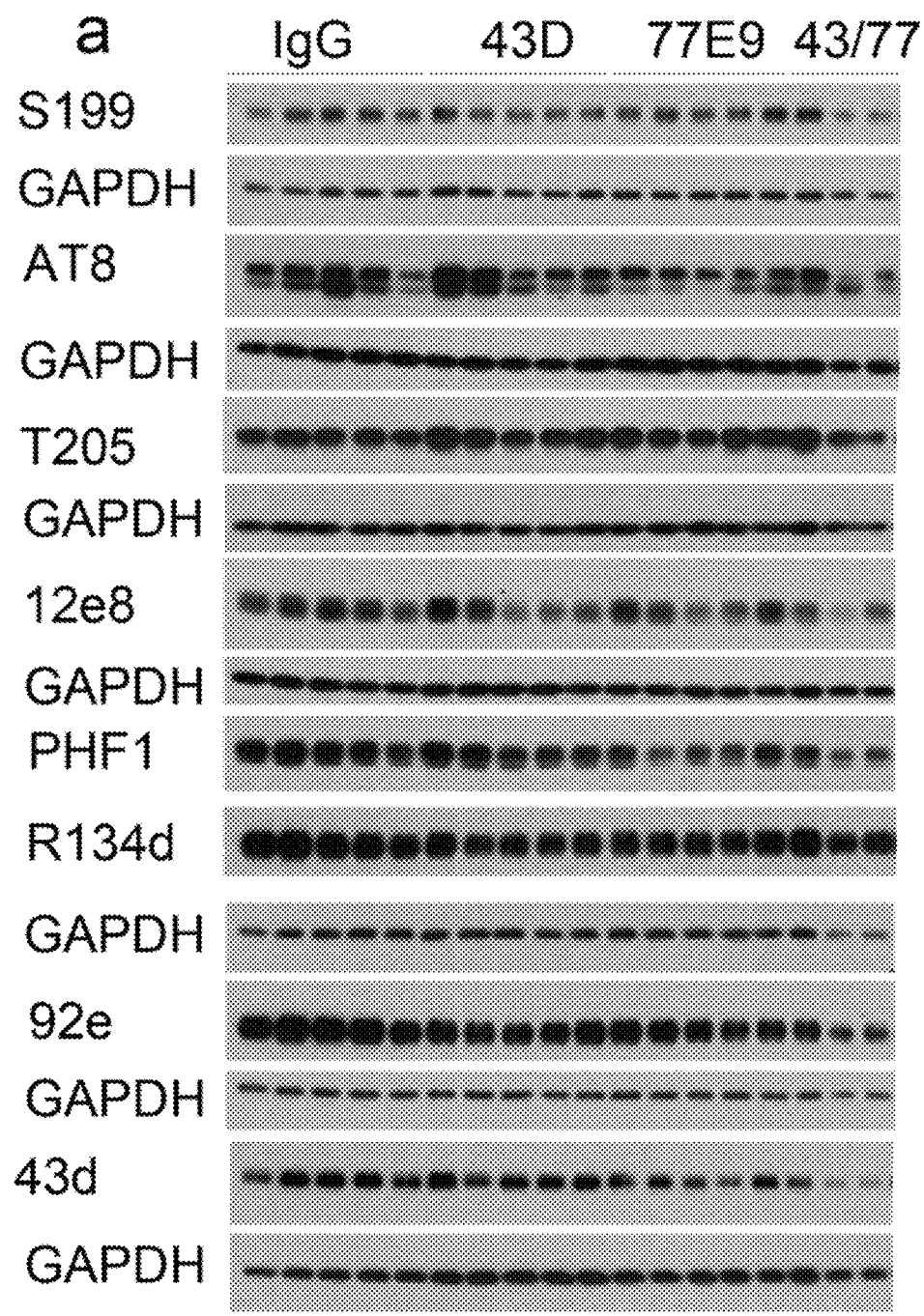
Figures 6B, 6C, 6D, 6E:
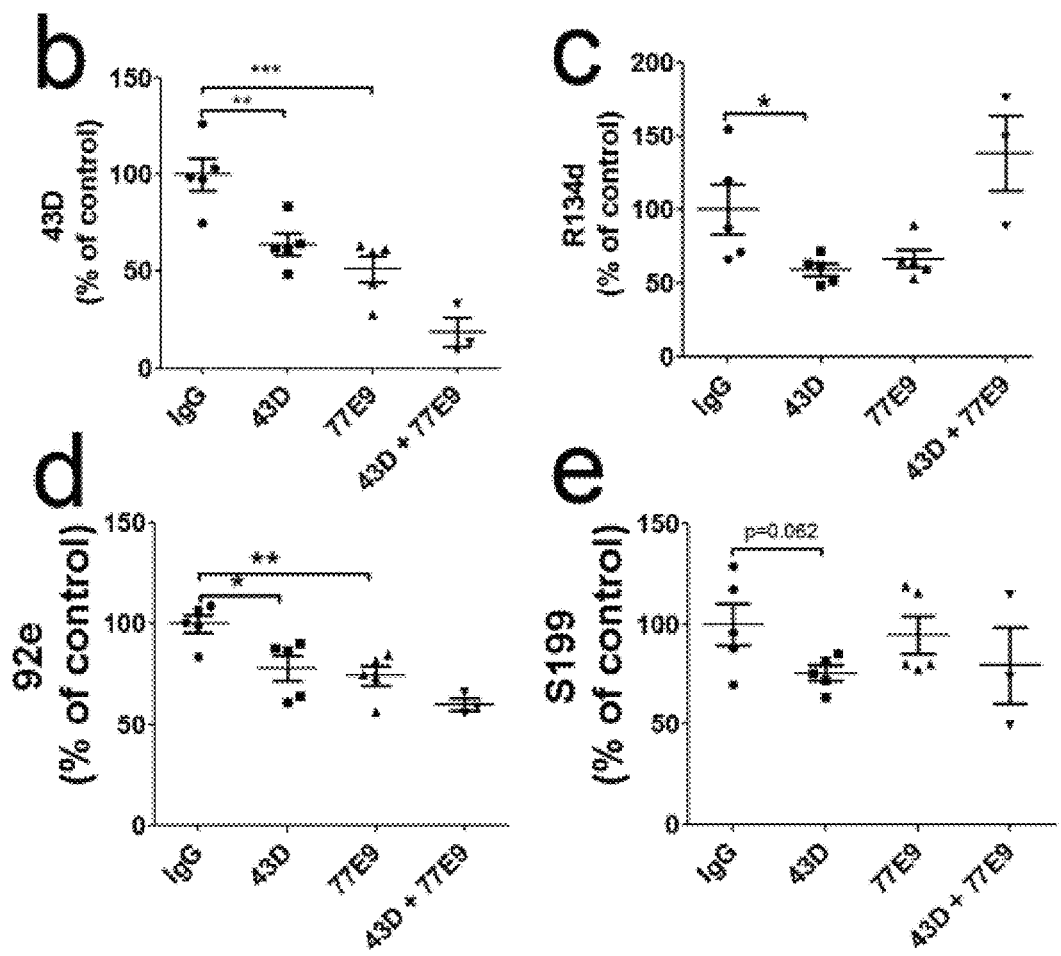
Figures 6F, 6G, 6H:
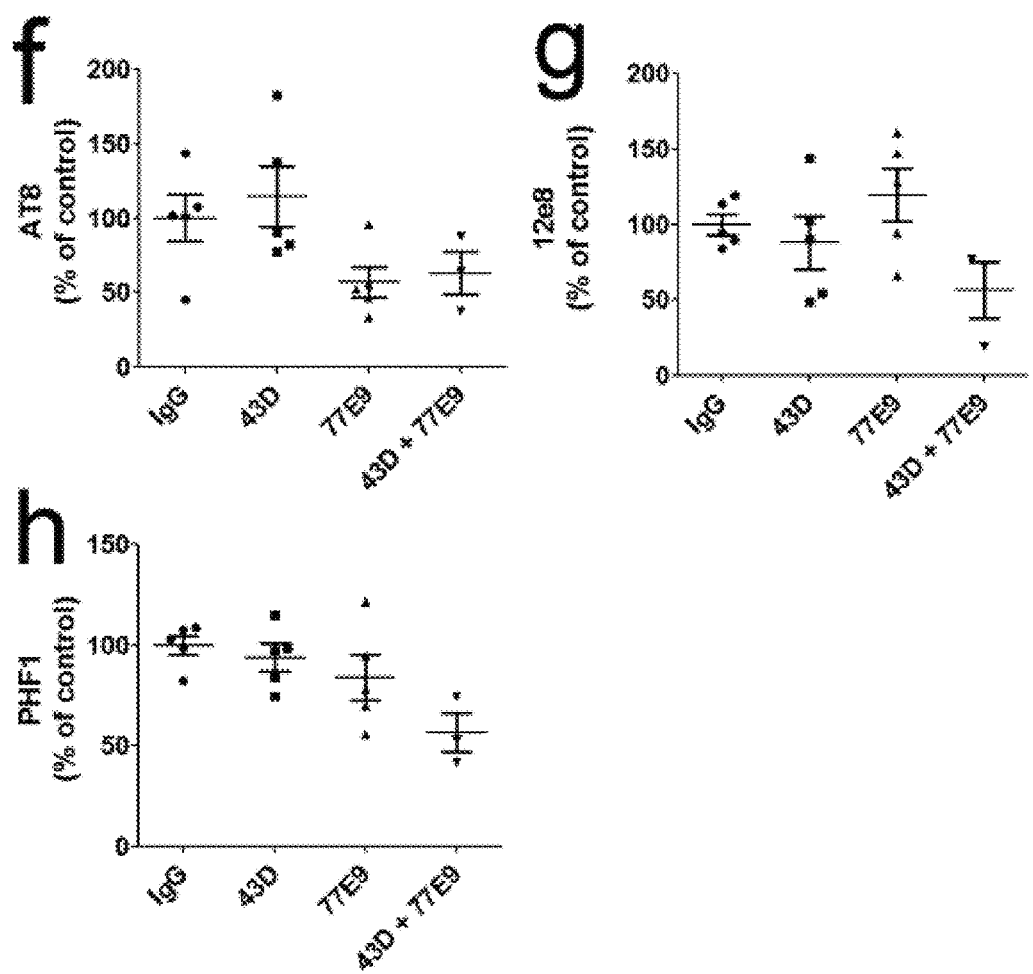

FIG. 6(a) is representative Western blots of hippocampus developed with R134d and 92e against total tau, 43D against human (transgenic) tau and several phosphorylation-dependent and site-specific tau antibodies showing that passive immunization with 2 doses of 43D or 77E9 antibodies reduced the levels of total tau but not hyperphosphorylated tau in hippocampus of 3×Tg-AD mice.

FIGS. 6(b) through (f) and FIGS. 6(f) through 6(h) are a series of graphs showing densitometrical quantification of blots after normalized with the GAPDH levels. Data are percentage of mouse IgG (100%)-treated animals reported as mean±SEM. *p<0.05, p<0.01*p<0.001 by ANOVA followed by a Bonferroni's posthoc test.

Figure 7A:
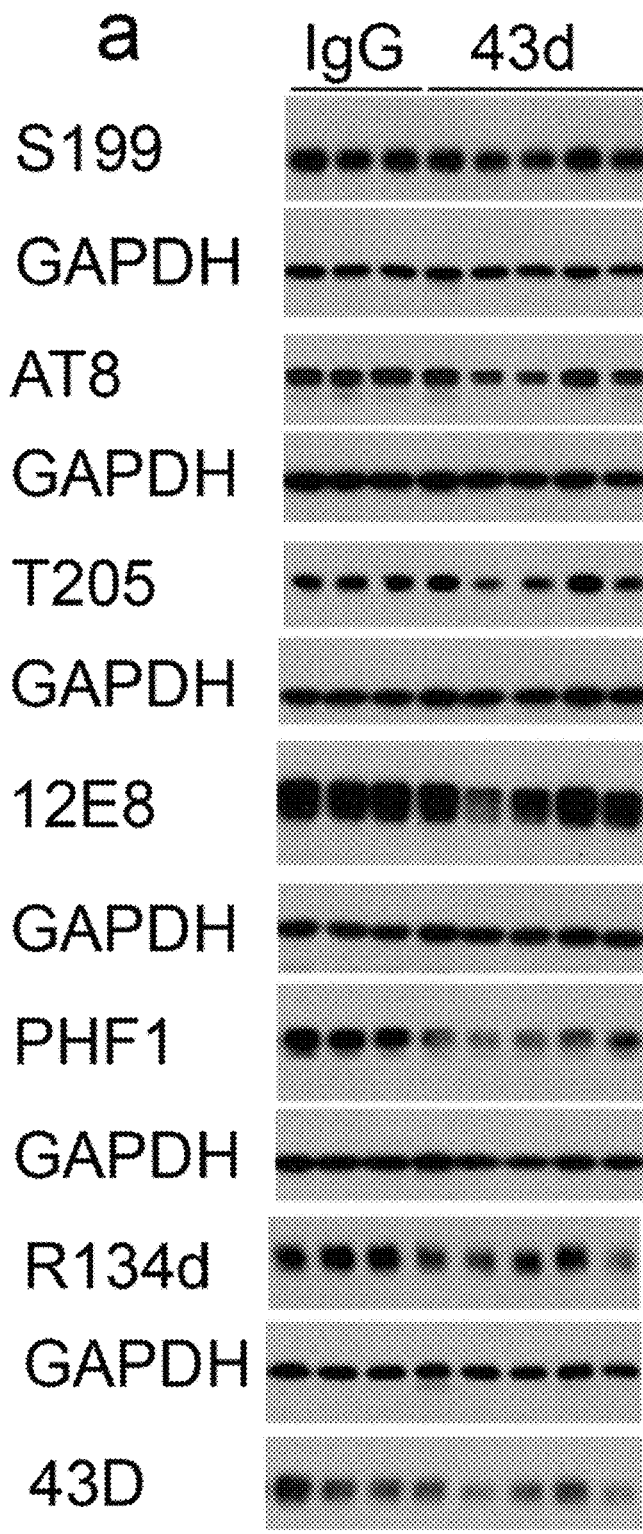

FIG. 7(a) is a representative Western blots of the hippocampus developed with R134d against total tau, 43D against human (transgenic) tau and several phosphorylation-dependent and site-specific tau antibodies showing passive immunization with 6 doses of 43D antibody reduced tau pathology in the hippocampus of 3×Tg-AD mice.

FIGS. 7(b) through 7(e) and FIGS. 7(f) through 7(h) are densitometrical quantification of blots after normalized with the GAPDH levels. Data are percentage of mouse IgG (100%)-treated animals reported as mean±SEM. *p<0.05, p<0.01* by unpaired two-tailed t test.

Figure 8A:
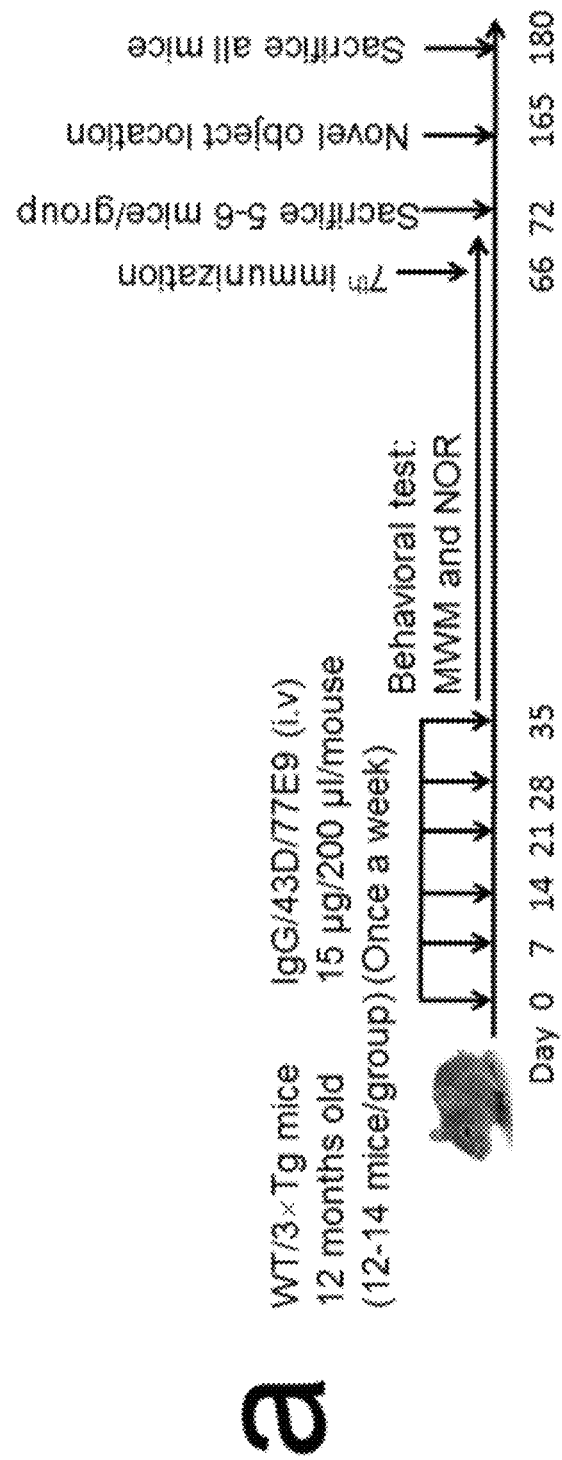

FIG. 8(a) is a graph of passive immunization with tau antibodies 43D and 77E9 improves cognitive performance without any side effects in 3×Tg-AD mice, where 3×Tg-AD mice were subjected to Morris water maze and one-trial novel object recognition task after immunization with 6 doses of mouse IgG, 43D, 77E9, or combination of 43D and 77E9 antibodies. On day 66, the mice were given 7$^{th}$ immunization and 5-6 mice per group were sacrificed on day 72. Novel object location test was carried out from day 165 to day 167 and all remaining mice were sacrificed on day 180. WT mice immunized with mouse IgG or combination of 43D and 77E9 were used as control.

FIGS. 8(b) through 8(e) and FIGS. 8(f) through 8(g) are a series of charts of (b) the body weights of the mice were measured once a week, (c) the escape latency (sec) to reach the hidden platform during acquisition phase for 5 days, (d) the percent time in the quadrant during the probe trial, (e) the number of target crossings in the probe trial, (f) the latency to first entrance into target zone, and (g) the average swim speed during the probe trial. Data are reported as mean±SEM. *p<0.05, p<0.01, *p<0.001 vs. control mice by two-way ANOVA followed by a Bonferroni's posthoc test.

Figures 9A, 9B:
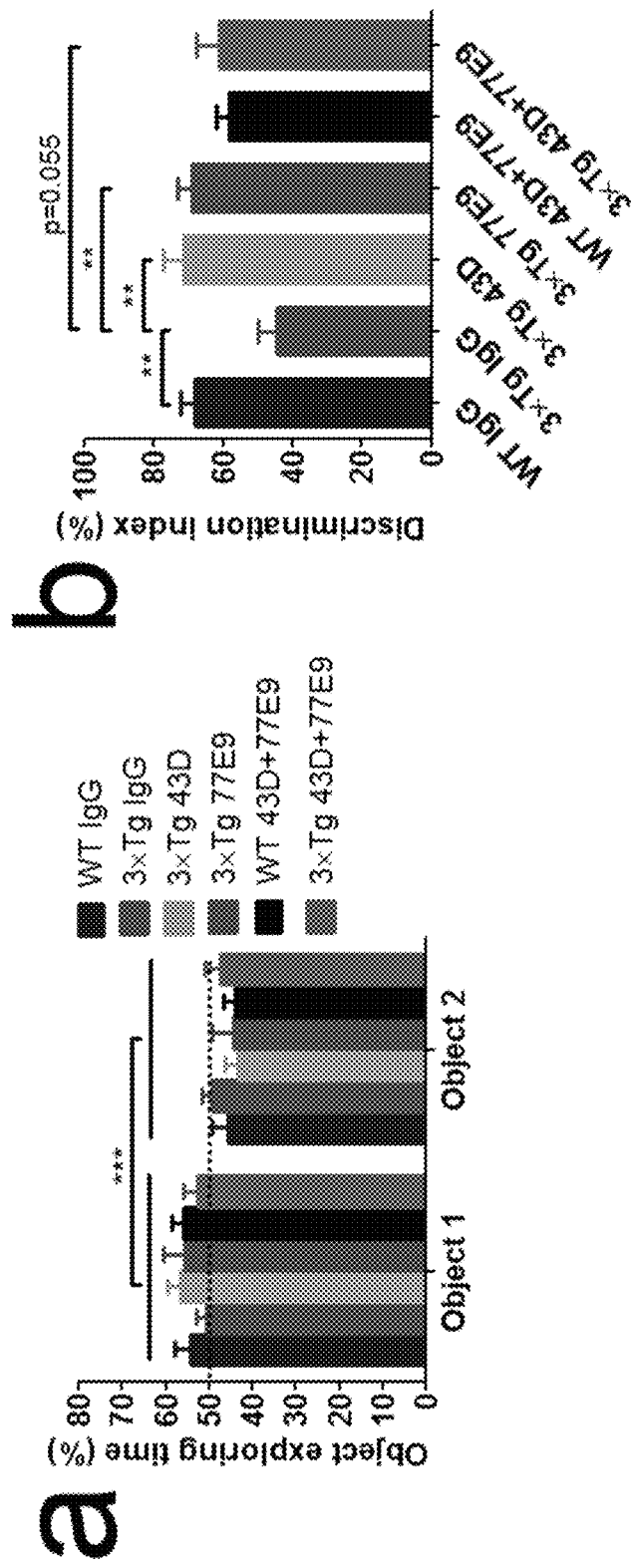

FIGS. 9(a) and 9(b) are a graphs of passive immunization with tau antibodies 43D and 77E9 improves short-term cognitive performance in 3×Tg-AD mice where, after four consecutive days of habituation (10 min per day) in an open field apparatus, the test phase (5 min) was carried out at 15 min after the sample phase (8 min) on 5$^{th}$ day, with the results showing: (a) the percent time spent exploring two identical objects during sample phase, and (b) the discrimination index (time exploring novel object/time exploring novel and familiar objects) in the test phase. Data are reported as mean±SEM. p<0.01, *p<0.001 vs. control mice by two-way ANOVA followed by a Bonferroni's posthoc test.

Figures 10A, 10B:
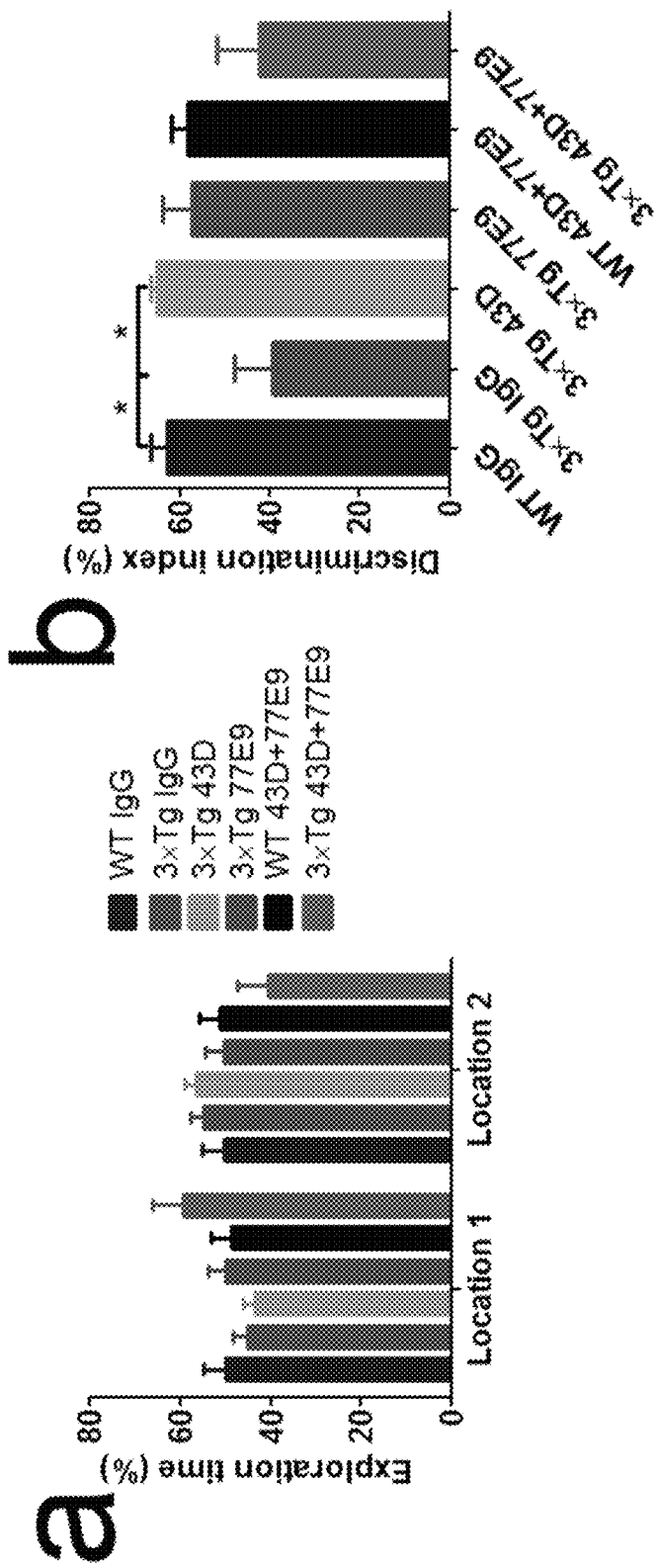

FIGS. 10(a) and 10(b) are graphs showing that passive immunization with tau antibodies 43D and 77E9 improves short-term cognitive performance in 3×Tg-AD mice for longer time. After two days of habituation (10 min per day) in an open field apparatus, the test phase (5 min) was carried out at 15 min after the sample phase (8 min) on 3$^{rd}$ day. FIG. 10(a) shows the percent time spent exploring two identical objects during sample phase, and FIG. 10(b) shows the discrimination index (time exploring object at novel location/time exploring novel and familiar locations object) in test phase. Data are reported as mean±SEM. p<0.01, *p<0.001 vs. control mice by two-way ANOVA followed by a Bonferroni's posthoc test.

Figure 11A:
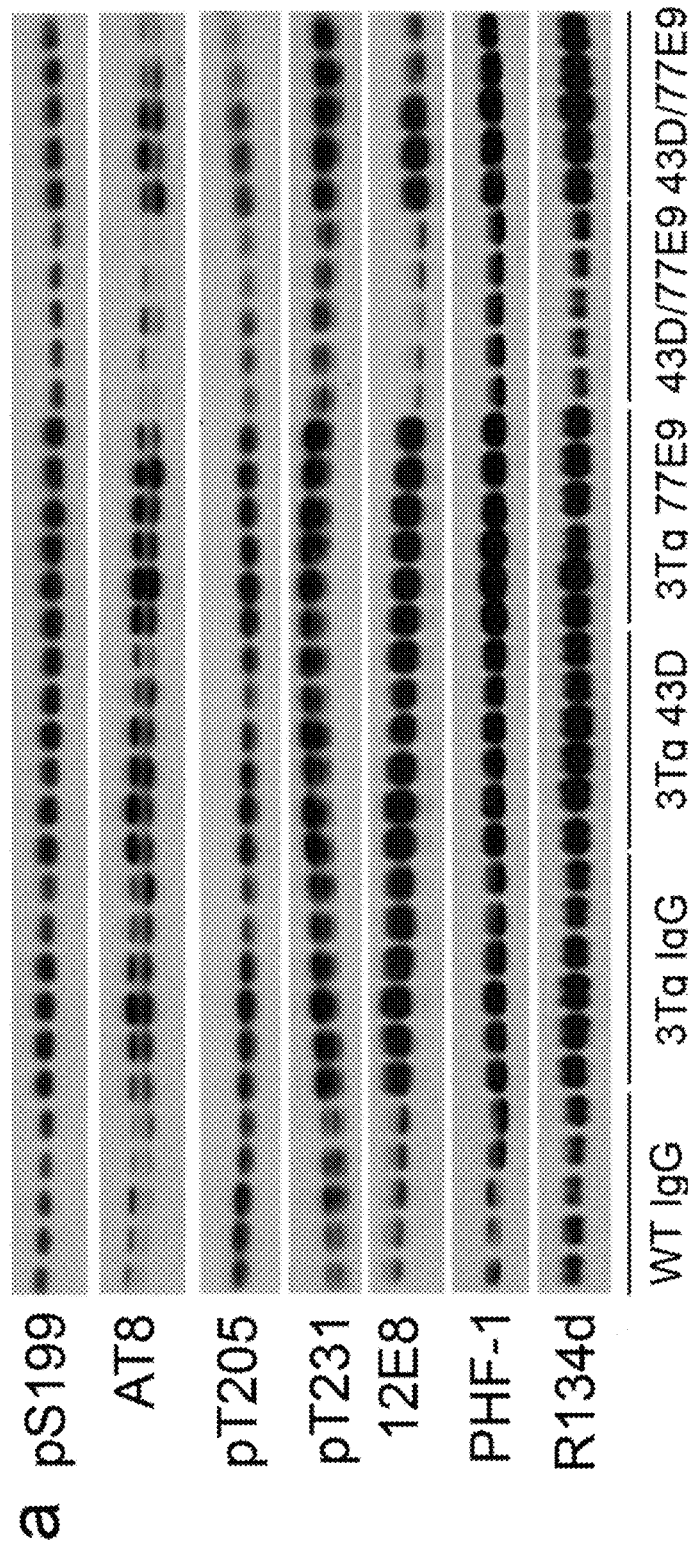
Figures 11D, 11E:
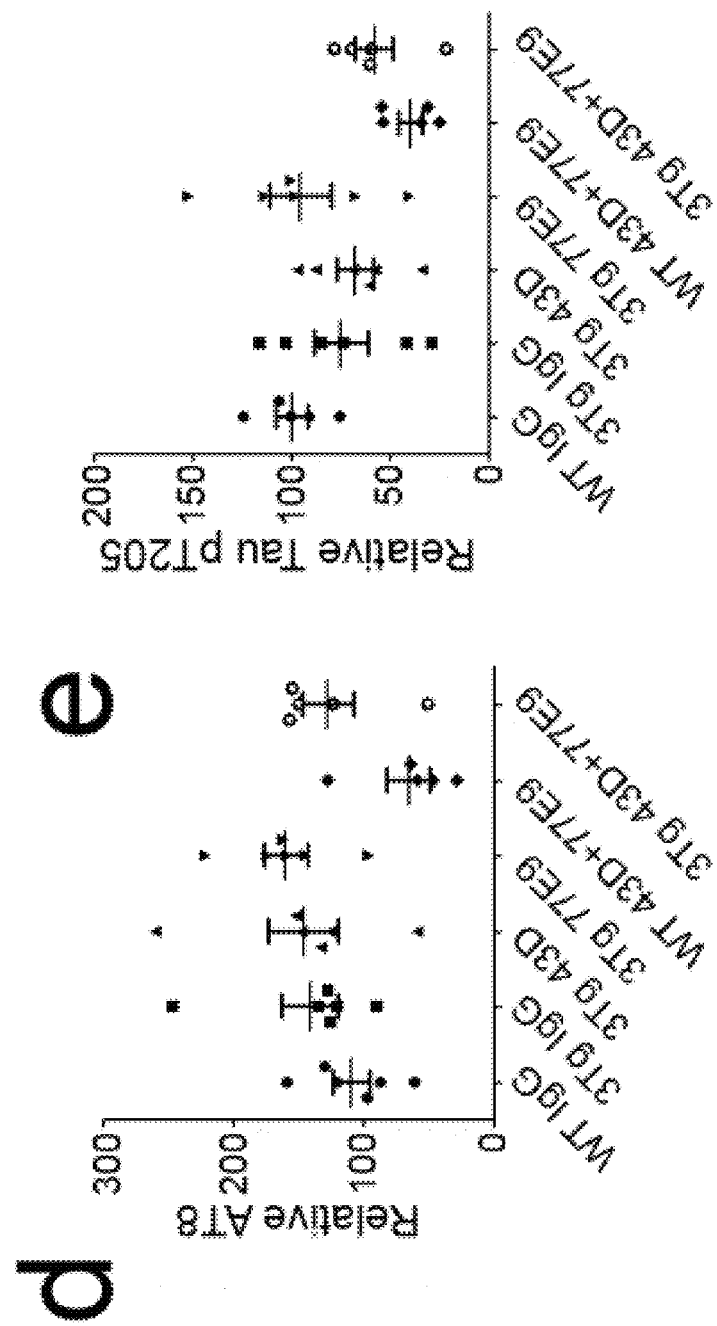
Figures 11F, 11G, 11H:
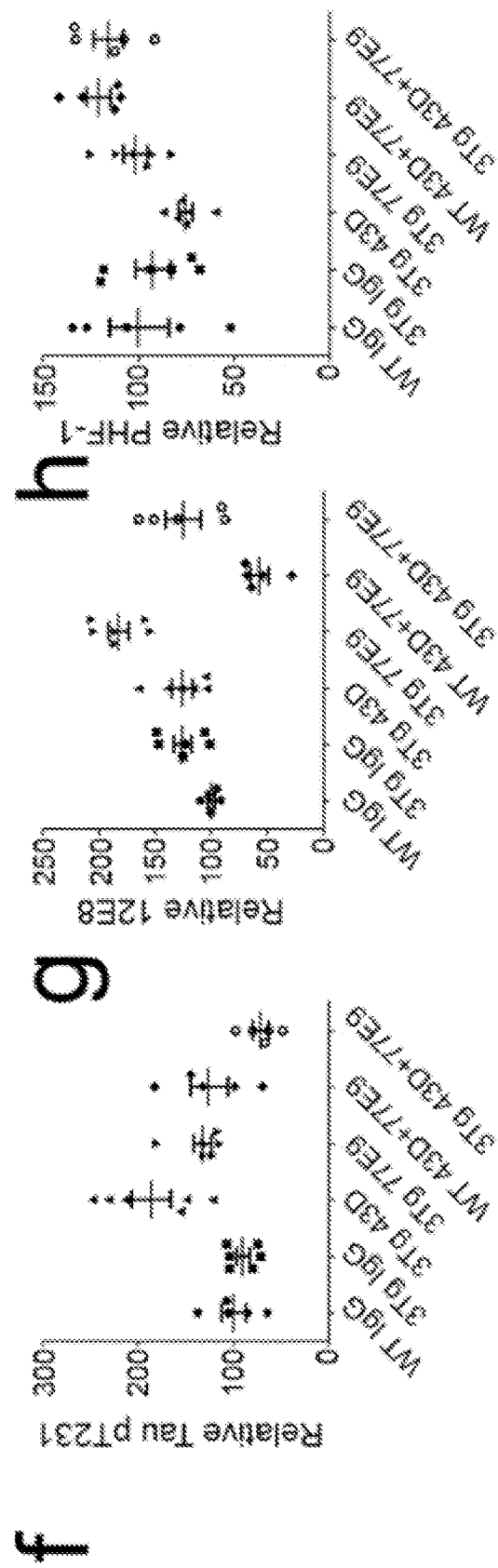

FIG. 11(a), FIGS. 11(b) and 11(c), FIGS. 11(d) and 11(e), and FIGS. 11(f) through 11(h) are a series of graphs showing that the long term effect of passive immunization with 43D and 77E9 antibodies on tau pathology are undetectable in the forebrain by Western blots five weeks after the sixth immunization. FIG. 11(a) are representative Western blots of forebrain developed with R134d against total tau, and several phosphorylation-dependent and site-specific tau antibodies. FIGS. (b) through (h) are densitometrical quantification of blots after normalized with the GAPDH levels. Data are percentage of mouse IgG (100%)-treated animals reported as mean±SEM. *p<0.05, p<0.01* by unpaired two-tailed t test.

FIGS. 12(a) through (c) and FIGS. 12(d) through 12(f) are graphs showing that passive immunization with 43D and 77E9 antibodies does not significantly affect the levels of Aβ40, Aβ42, and the ratio of Aβ42/Aβ40 in forebrain. The level of Aβ40 and Aβ42 in forebrain were quantified by ELISA at 5 weeks, FIGS. 12(a) through (c), or 5 months, FIGS. 12(d) through 12(e), after the sixth immunization with 43D and 77E9 antibodies. Data are shown as mean±SEM.

DETAILED DESCRIPTION OF THE INVENTION

The present invention comprising the use of antibodies targeting the amino terminal region of human tau (amino acid residues 6-18) can reduce total tau levels, decrease tau hyperphosphorylation, and improve reference memory. In order to determine the efficacy of the invention, the effects of both the antibody specific to the amino terminal region of human tau and an antibody targeting a more distal amino terminal projection in tau were administered to aged 3×Tg-AD mice at moderate to severe stages of pathology. While passive immunization with both antibodies reduced total tau and tau hyperphosphorylated at several sites, a non-significant trend to reduce Aβ pathology, the immunization with antibody 43D targeting tau 6-18, but not 77E9 targeting tau 184-195 improved cognition in aged 3×Tg-AD mice.

Example 1

Materials and Methods
Antibodies and Reagents
Primary antibodies used in this study are listed in Table 1 below:

TABLE 1

| Antibody | Type | Specificity | Phosphorylation sites | Source/reference |
|---|---|---|---|---|
| 43D | Mono- | Tau | | Covance |
| 77 E9 | Mono- | Tau | | Covance |
| R134d | Poly- | Tau | | J Neurosci 19 (13): 5245-5254. |
| GAPDH | Poly- | GAPDH | | Santa Cruz Biotechnology |
| pS199 | Poly- | P-tau | Ser199 | Invitrogen |
| AT8 | Mono- | P-tau | Ser202/Thr205 | Thermo Fisher Scientific |
| pT205 | Poly- | P-tau | Thr205 | Invitrogen |
| 12 E8 | Mono- | P-tau | Ser262/356 | Dr. D. Schenk, Elan Pharmaceuticals |
| PHF-1 | Mono- | P-tau | Ser396/404 | Dr. P. Davies, AECOM |

Tau antibodies 43D against tau 6-18 epitope and 77E9 against tau 184-195 epitope were generated at New York State Institute for Basic Research, Staten Island. Peroxidase-conjugated anti-mouse and anti-rabbit IgG were obtained from Jackson ImmunoResearch Laboratories (West Grove, Pa., USA). The enhanced chemiluminescence kit was from Pierce (Rockford, Ill., USA). Human Aβ1-40 enzyme-linked immunosorbent assay (ELISA) kits were from Invitrogen (Carlsbad, Calif., USA). DPBS buffer was from Thermo-Scientific, MA, USA. Other chemicals were from Sigma (St. Louis, Mo., USA).

Animal studies were approved by the Institutional Animal Care and Use Committee (IACUC) and were according to US PHS NIH guidelines. The aged female 3×Tg-AD mice harboring PS1M146V, APPSWE, and tauP301L transgenes, created in the laboratory of Dr. Frank LaFerla, represent one of the most biologically relevant mouse models for AD. These mice develop amyloid plaques starting at 6 months of age and NFTs starting 12 months age, respectively, where the pathologies are predominantly restricted to the hippocampus, amygdala, and the cerebral cortex. The female 3×Tg-AD mice (9-10 mice/group) were injected at 14-17 months of age intraperitoneally (i.p.) with 100 µg of antibody 43D or 77E9 antibodies in 100 µL saline once a week for 4 weeks. Mice treated identically but with vehicle (saline) only or mouse IgG in saline were treated as controls. One day after the fourth injection the animals were tested for spatial learning and memory by Morris water maze task. At the end of the reference memory test mice were sacrificed, one half of the brain was fixed in 4% paraformaldehyde for histological and immunohistological studies, and the other half was dissected into hippocampus and cerebral cortex and saved at −75° C. for biochemical analysis (FIG. 1a).

A general examination of all the mice was conducted in the home cages throughout the whole study. Any gross abnormalities in overall health, home cage nesting, sleeping, feeding, grooming, and condition of the fur of animals were noted; body weight was measured once a week.

Morris Water Maze

Morris water maze (MWM) task was used to evaluate spatial learning and memory of the mice. The test was performed in a circular white pool (with a diameter of 180 cm and a height of 60 cm) filled with white dye tinted water and maintained at room temperature (20±1° C.). The maze was designated of two virtual principal axes with each line bisecting the maze perpendicular to the other one to divide the maze into four equal quadrants. The end of each line demarcates four cardinal points: north (N), south (S), east (E) and west (W). A platform was positioned in the middle of one of the quadrants submerged 1 cm below water surface. Each mouse performed 4 trials per day for 4 consecutive days from semi-random start positions to find the hidden platform. Each trial was terminated as soon as the mouse climbed onto the hidden platform. If a mouse failed to find the platform within 90 sec, it was gently guided to it. At the end of each trial, the mouse was left on the platform for 20 sec, then removed, dried and returned it to its home cage. A 60 sec probe test without platform was performed 24 hours after the last trial. The swim path, swim distance (cm), escape latency (sec), swim speed (cm/sec), time spent in each quadrant (sec), and distance traveled in each quadrant (cm) were recorded through an automated tracking system (Smart video tracking system, version 2.0.14, Panlab; Harvard Apparatus).

Tissue Processing

After completion of the Morris water maze task, all mice were sacrificed by cervical dislocation. Forebrain cortex and hippocampus were detached immediately from the left hemisphere and frozen in dry ice for biochemical analysis. The right hemisphere was fixed in 4% paraformaldehyde in 100 mM phosphate buffered saline (PBS) for at least 24 hours at room temperature. Tissues were then post-fixed in a 30% sucrose solution at 4° C. □□ for overnight. Forty µm sagittal sections of the entire half hemisphere were cut using a freezing microtome. The sections were stored in glycol anti-freeze solution (ethylene glycol, glycerol and 100 mM PBS in 3:3:4 ratio) at −20° C. until further processing.

Human Aβ40 Measurements by ELISA

The tissue from forebrain cortex was homogenized in 10 volumes of ice-cold guanidine hydrochloride buffer (50 mM Tris-HCl, pH 8.0, 5.0 M guanidine.HCl). The homogenate was mixed for 4 hours at room temperature, and then stored at −20° C. For ELISA, each brain homogenate was diluted 1:25 with ice-cold reaction buffer (5% BSA, 0.03% Tween-20, 2.1 mM AEBSF, 20 µg/ml aprotinin, 20 µg/ml leupeptin, 2.0 mM EDTA, pH 7.4] in DPBS (ThermoScientific, prod #28344) and centrifuged at 16,000×g for 20 min at 4° C. The final concentration of AEBSF was 1 mM to prevent proteolysis of the Aβ peptides, and the final concentration of guanidine hydrochloride was 0.1 M. The supernatant was further diluted 1:1(v/v) with standard diluent buffer and assessed using ELISA kit specific for Human Aβ40 and calibrated with synthetic Aβ peptides from Invitrogen (Cat #KHB3482) according to the manufacturer's instructions. The Aβ40 peptide standards were prepared with the same composition of the buffer used for the dilution of the samples.

Western Blot Analysis

Mouse brain tissue was homogenized in pre-chilled buffer containing 50 mM Tris-HCl, pH 7.4, 0.25 M sucrose, 2 mM EDTA, 10 mM β-mercaptoethanol, 0.5 mM AEBSF, 10 µg/ml aprotinin, 10 µg/ml leupeptin, 4 µg/ml pepstatin, 5 mM benzamidine, 20 mM β-glycerophosphate, 50 mM sodium fluoride, and 1 mM sodium vanadate. Each homogenate was boiled in Laemmli's buffer for 5 min and protein concentration was measured by modified Lowry method. The samples were resolved in 10% or 12.5% SDS-PAGE and electro-transferred onto Immobilon-P membrane (Millipore, Bedford, Mass., USA). The blots were then probed with primary antibody (as seen in Table 1) and developed with the corresponding horseradish peroxidase-conjugated secondary antibody and ECL kit (Pierce, Rockford, Ill.). Densitometrical quantification of protein bands in Western blots were analyzed by using the Multi Gauge V3.0 software (Fuji Photo Film Co., Ltd).

Immunohistochemical Staining

Immunohistochemical quantification of abnormally hyperphosphorylated tau was performed on 3-4 sections from minimum 4 mice per group. Free-floating sagittal sections were washed in 10 mM PBS (15 min×3) and then incubated in 0.5% Triton X-100 for 20 min. The sections were again washed in 10 mM PBS (15 min×3) and blocked in a solution containing 5% normal goat serum and 0.1% Triton X-100 for 30 min. Sections were then incubated at 4° C. overnight with the mouse monoclonal antibody AT8 which recognizes tau phosphorylation at Ser202/Thr 205 (1:500, ThermoScientific, Rockford, Ill., USA). The next day, after washing three times for 15 min with 10 mM PBS, Alexa 488-conjugated goat anti-mouse IgG antibody (1:500, Molecular Probes, Carlsbad, Calif., USA) in 10 mM PBS with 0.05% Tween-20 was used as secondary antibody for 2 hours at room temperature. Sections were subsequently washed, mounted, and cover slipped using Fluorogel mounting medium (Electron Microscopy Sciences, Hatfield, Pa., USA). Only brain regions showing overt positive specific staining, namely the CA1 of the hippocampus and the subiculum, were evaluated. Maximum projection images were generated based on confocal z-stacks using Nikon 90i fluorescent microscope equipped with Nikon C1 three-laser confocal system and a Nikon DS U1 digital camera. The AT8 immunoreactive load was quantified using NIH Image J (v.1.46r) as described previously.

For thioflavin-S positive (TS+) plaque load quantification, 5-7 serial sections were selected from minimum 4 mice per group. Thioflavin-S staining was performed as described before. Briefly, free floating brain sections were rinsed in water for 6 min and then incubated in 0.25% KMnO4 for 4 min. Sections were washed in water for another 6 min, and incubated in 1% K2S2O5 and 1% oxalic acid until the brown color completely faded. Sections were stained with 0.05% thioflavin-S in water in dark for 8 min. Finally, sections were wash in 80% ethanol for 2 min and in water for 3 min, and mounted and cover slipped using Fluorogel mounting medium (Electron Microscopy Sciences, Hatfield, Pa., USA). The maximum projection images were taken and TS+ plaque load was quantified in hippocampus CA1 and subiculum using NIH Image J (v.1.46r).

Statistical Analysis

Data were analyzed using GraphPad Prism version 5.0 (GraphPad Software Inc, La Jolla, Calif., USA) and one-way or two-way ANOVA (as appropriate) followed by a Bonferroni's posthoc test. Further intergroup comparisons were also performed using un-paired two-tailed t-test. All data are presented as means±SEM, and $p<0.05$ was considered statistically significant.

Results

Passive immunization with antibodies targeting the N-terminal projection domain of tau reduces both total and hyperphosphorylated tau in aged 3×Tg-AD mice.

Triple transgenic AD mice are known to develop tau pathology starting around 12 months of age which is first apparent in the hippocampus and then progresses to the cerebral cortex. To assess whether passive immunization with tau antibodies 43D against tau 6-18 and 77E9 against tau 184-195 reduces tau pathology in aged 3×Tg-AD mice, the level of tau phosphorylated at Ser202/Thr205 sites was first determined with AT8 antibody by immunohistochemistry, as seen in FIG. 1. Passive immunization with antibody 43D and 77E9 antibodies dramatically decreased tau hyperphosphorylation at Ser202/Thr205 in subiculum and CA1 area, as seen in FIG. 1(b)-(d).

Furthermore, the levels of total and hyperphosphorylated taus by Western blots was investigated and it was found that passive immunization with 77E9 antibody significantly reduced levels of both total tau (R134d) and its hyperphosphorylation at Ser199, Ser202/Thr205 (AT8), Thr205, Ser262/356 (12E8) and Ser396/404 (PHF-1) sites in hippocampus compared with mouse IgG-treated control animals. Immunization with 43D against tau 6-18 also showed a decrease in total tau level, though this reduction did not reach statistical significance and significantly decreased tau phosphorylation at Ser199, Ser202/Thr205 (AT8), Ser262/356 (12E8) and Ser396/404 (PHF-1) sites with the exception at Thr205 site, as seen in FIG. 2. Similar results were found in forebrain cortex, as seen in FIG. 3. Especially, passive immunization with 43D antibody also decreased tau phosphorylation at Thr205 site in forebrain cortex. Interestingly, passive immunization targeting tau 184-195 by 77E9 decreased more total and hyperphosphorylated taus than that by 43D antibody, as seen in FIGS. 2 and 3. All together, this data clearly indicates that immunization targeting tau 6-18 and tau 184-195 can dramatically reduce tau pathology.

It was also determined that passive immunization with tau antibodies does not affect Aβ accumulation in moderate to severe stage of plaque pathology. Triple transgenic AD mice develop amyloid plaques starting around 6 months of age which is first apparent in the cortex and progresses to the hippocampus with age. An investigation was performed whether passive immunization with tau antibodies 43D and 77E9 could alter the level of Aβ. Immunization with tau antibodies targeting tau 6-18 and tau 184-195 epitopes does not affect amyloid plaque load in subiculum and CA1 region, as seen in FIG. 4(a)-(c). In line with the immunohistochemistry results, the level of Aβ1-40 determined by ELISA was similar among 43D, 77E9 and mouse IgG treated mice, as seen in FIG. 4(d). These data suggests that immunotherapy targeting tau 6-18 or tau 184-195 does not have a significant effect on the amyloid plaque load in aged 3×Tg-AD mice.

Passive immunization with tau antibodies targeting the N-terminal projection domain of tau does not affect the general behavioral phenotypes in aged 3×Tg-AD mice. During the 5-week period of the study, the general condition of mice were carefully monitored daily and the mice were weighed once a week. No abnormality was noted in general physical characteristics, including grooming, posture, and clasping reflex. Immunization with 43D and 77E9 did not cause significant change in body weight, as seen in FIG. 5(a). These data indicate that passive immunization targeting N-terminal tau 6-18 by 43D and tau 184-195 by 77E9 does not cause any neurological deficits in aged female 3×Tg-AD mice.

Passive immunization with tau antibodies targeting the N-terminal projection domain of tau improves cognitive performance in aged 3×Tg-AD mice. Triple transgenic AD mice are known to show strong deficits in learning and memory in the Morris water maze task starting at 6 months of age. In the present study, the animals were subjected to Morris water maze task to determine the effect of passive immunization with tau antibodies on the spatial reference memory. 3×Tg-AD mice treated with 43D antibody took significant less time than control mice to find the hidden platform, as seen in FIG. 5(b), in acquisition phase. More importantly, in the probe trial, 3×Tg-AD mice treated with 43D antibody also spent a significant longer time than control mice in the target quadrant that formerly contained the platform, as seen in FIG. 5(c). Unlike the mice treated with 43D antibody, the performance of 3×Tg-AD mice treated with 77E9 was similar to that of control mice, as seen in FIGS. 5(b) and (c). Additionally, no significant difference was observed in swim speed, as seen in FIG. 5(d), and distance covered, as seen in FIG. 5(e), during probe trial among 43D, 77E9 and saline-treated 3×Tg-AD mice. These data demonstrate that passive immunization with tau antibodies 43D against N-terminal projection domain tau 6-18, but not 77E9 targeting tau 184-195 could improve cognitive performance in aged 3×Tg-AD mice.

Treatment of aged 3×Tg-AD mice with antibodies 43D against tau 6-18 and 77E9 against tau 184-195 once a week for 4 weeks revealed that that passive immunization targeting tau 6-18 and tau 184-195 both decreased total tau and tau hyperphosphorylated at Ser199, Ser202/Thr205 (AT8), Thr205, Ser262/356 (12E8) and Ser396/404 (PHF-1) sites in the forebrain. Most importantly, 3×Tg-AD mice treated with 43D antibody showed better performance in Morris water maze task than the saline-treated control mice, which indicates that immunotherapy targeting normal N-terminal projection domain of tau, tau 6-18 improves cognition in aged 3xTg-AD mice. On the contrary, targeting tau 184-195 reduced levels of hyperphosphorylated tau, but failed to rescue cognitive deficits. Immunization with these two antibodies showed a trend but did not significantly reduce Aβ accumulation in the aged 3xTg-AD mice. Although this finding is consistent with a study that showed that tau pathology precedes Aβ pathology in aged and AD brains, the mechanism by which tau immunotherapy may influence Aβ pathology is unknown. The reduction in Aβ pathology may be due to proteolysis of Aβ as a bystander effect of the activation of the complement system produced by tau immunization. However, a reduction of APP synthesis and or its amyloidogenic processing are other possibilities which, at present, cannot be ruled out.

The present invention is the first to decrease Aβ and plaque load by tau immunotherapy in a mouse model. Indeed, accumulating evidence from preclinical studies indicates that pathological tau based immunotherapy decreases the tau pathology and rescues the functional impairment. The present invention has shown that antibodies to N-terminal projection domain of tau 6-18 and tau 184-195 not only decrease total tau level, but also dramatically reduce the hyperphosphorylated protein in the advanced stage of the pathology. In addition, immunization targeting tau 6-18 by 43D antibody, but not using anti-tau 184-195, improves cognition using Morris water maze task, which suggests that the tau epitope specificity is important for tau based immunotherapy to prevent or attenuate the cognitive decline. Thus, immunotherapy targeting tau 6-18 epitope may present a promising therapeutic opportunity for AD patients and patients with other tauopathies.

Tau is a highly soluble, natively unfolded microtubule-associated protein that normally promotes tubulin assembly, microtubule stability, and cytoskeletal integrity. Therefore, another major concern associated with tau based immunotherapy is potential toxicity because of cellular uptake of antibodies and binding to normal tau may result in destabilization of the microtubules and subsequent interference with axonal transport and cytoskeletal integrity. The present invention considered 43D and 77E9 targeting tau 6-18 and tau 184-195, respectively. The different specificity of targeting tau epitope by 43D and 77E9 may be one possible explanation for the finding that immunization with 77E9 antibody reduced more both total tau and the hyperphosphorylated protein than 43D antibody at most of the tested phosphorylation sites, but treatment with 43D antibody and not 77E9 improved cognition in aged 3xTg-AD mice. This discrepancy could be due to neutralization of the beneficial effect of immunization with 77E9 antibody by its toxicity, though significant abnormality in general physical characteristics was not observed, including grooming, posture, and clasping reflex. The therapeutic beneficial effect of passive immunization with tau antibody 43D to tau 2-18 that was found is consistent with a toxic domain in this region of the protein. However, without testing experimentally, it is not possible to predict whether immunotherapy with tau 19-230 will be neuroprotective or deleterious and mediate Aβ toxicity. However, no deleterious effect of immunization with antibody 77E9 to tau 184-195 was observed.

Thus, passive immunization targeting N-terminal projection domain of tau 6-18 and tau 184-195 with 43D and 77E9 antibodies once a week for 4 weeks can effectively decrease both total and hyperphosphorylated taus at an advanced stage of the disease in 3xTg-AD mice. Importantly, short-term treatment with 43D antibody targeting tau 6-18 rescued cognitive impairments possibly by reduction of the neurotoxic region of tau. The passive immunization targeting N-terminal projection domain of tau, however, had a trend but no statistically significant ameliorating effect on the advanced stage Aβ pathology in the transgenic mice. Thus, passive immunization targeting the N-terminal projection domain of tau can present a promising treatment opportunity for AD, targeting a normal tau epitope can effectively clear the hyperphosphorylated tau, and more attention should be paid to select the effective tau epitopes for targeting.

Example 2

Materials and Methods

Antibodies and Reagents

Primary antibodies used in this study are listed in Table 2 below. Tau antibodies 43D against tau 6-18 epitope and 77E9 against tau 184-195 epitope were generated at New York State Institute for Basic Research, Staten Island. Peroxidase-conjugated anti-mouse and anti-rabbit IgG were obtained from Jackson ImmunoResearch Laboratories (West Grove, Pa., USA). The enhanced chemiluminescence kit was from Pierce (Rockford, Ill., USA). Human Aβ1-40 and human Aβ1-42 enzyme-linked immunosorbent assay (ELISA) kits were from Invitrogen (Carlsbad, Calif., USA). DPBS buffer was from Thermo Scientific, MA, USA. Other chemicals were from Sigma (St. Louis, Mo., USA).

TABLE 2

Primary antibodies

| Antibody | Type | Specificity | Phosphrylation sites | Source/reference |
|---|---|---|---|---|
| 43D | Mono- | Tau | | Covance |
| 77 E9 | Mono- | Tau | | Covance |
| R134d | Poly- | Tau | | J Neurosci 19 (13): 5245-5254. |
| GAPDH | Poly- | GAPDH | | Santa Cruz Biotechnology |
| pS199 | Poly- | P-tau | Ser199 | Invitrogen |
| AT8 | Mono- | P-tau | Ser202/Thr205 | Thermo Fisher Scientific |
| pT205 | Poly- | P-tau | Thr205 | Invitrogen |
| 12 E8 | Mono- | P-tau | Ser262/356 | Dr. D. Schenk, Elan Pharmaceuticals |
| PHF-1 | Mono- | P-tau | Ser396/404 | Dr. P. Davies, AECOM |

Mice and Antibody Injections

Animal studies were approved by our Institutional Animal Care and Use Committee (IACUC) and were according to US PHS NIH guidelines The homozygous 3xTg-AD mice harboring $PS1_{M146V}$, $APP_{SWE}$, and $tau_{P301L}$ transgenes under the control of the mouse Thy1.2 promoter in neurons, created in the laboratory of Dr. Frank LaFerla, represent one of the most biologically relevant mouse models for AD. These mice develop amyloid plaques starting at ~9 months of age and NFTs starting ~12 months age, respectively, where the pathologies are predominantly restricted to the hippocampus, amygdala, and the cerebral cortex.

3xTg-AD mice are maintained on a hybrid 129/Sv and C57BL/6 mice background and wildtype (WT) controls are of the same genetic background.

Tau Antibodies Immunizations

To investigate the dose dependent effect of passive immunization with N-terminal tau antibodies on reduction of tau pathology in 3xTg-AD mice, 3xTg-AD mice (4-5 mice/group) were immunized intravenously with 15 μg of mouse IgG, 43D, 77E9, and a mixture of 7.5 µg of 43D and 7.5 µg of 77E9 in 200 µL saline once a week for 2 weeks, or immunized with 15 µg of mouse IgG and 43D in 200 µL saline once weekly for 6 weeks. All animals were sacrificed for biological analysis 24 hours after last immunization. One half of the brain was fixed in 4% paraformaldehyde for histological and immunohistological studies, and the other half was dissected into hippocampus and cerebral cortex and saved at −75° C. until used for biochemical analysis.

To determine the beneficial effect of passive immunization with N-terminal tau antibodies on cognitive improvement in 3×Tg-AD mice, the 12 months old female 3×Tg-AD mice (12-14 mice/group) were immunized intravenously with 15 µg of mouse IgG, 43D or 77E9 antibodies, or mixture of 7.5 µg of 43D and 7.5 µg of 77E9 in 200 µL saline once a week for 6 weeks. WT mice treated identically with mouse IgG or mixture of 43D and 77E9 in 200 µL saline were used as controls. Behavioral tests were carried out on the day after the sixth injection. After behavioral tests, animals were immunized with one more dose on day 66, and 5-6 mice per group were sacrificed on day 72. The remaining mice were housed for another 3 months before they were sacrificed. One half of the brain was fixed in 4% paraformaldehyde for histological and immunohistological studies, and the other half was dissected into forebrain including hippocampus and cerebral cortex, and saved at −75° C. until used for biochemical analysis.

General Examination

A general examination of all the mice was conducted in the home cages throughout the whole study. Any gross abnormalities in overall health, home cage nesting, sleeping, feeding, grooming, and condition of the fur of animals were noted; body weight was measured once a week.

Morris Water Maze

Morris water maze (MWM) task was used to evaluate spatial learning and memory of the mice. The second day after the $6^{th}$ immunization, a total of 74 mice were subjected to Morris water maze testing. The test was performed in a circular white pool (with a diameter of 180 cm and a height of 60 cm) filled with white dye (non-toxic) tinted water and maintained at room temperature (20±1° C.). The maze was designated of two virtual principal axes with each line bisecting the maze perpendicular to the other one to divide the maze into four equal quadrants. The end of each line demarcates four cardinal points: north (N), south (S), east (E) and west (W). A platform was positioned in the middle of one of the quadrants submerged 1 cm below water surface. Each mouse performed 2 trials on day 1 and 2, 3 trials on day 3, 4 trials on day 4 and 5 for 5 consecutive days from semi-random start positions to find the hidden platform. Each trial was terminated as soon as the mouse climbed onto the hidden platform. If a mouse failed to find the platform within 90 sec, it was gently guided to it. At the end of each trial, the mouse was left on the platform for 20 sec, then removed, dried and returned it to its home cage. A 90 sec probe test without platform was performed 24 hours after the last trial. Escape latency (sec) and swim speed (cm/sec) in initial training, and latency to $1^{st}$ entrance into target, target crossings, swim speed (cm/sec) and time spent in each quadrant (sec) in probe test were recorded through an automated tracking system (Smart video tracking system, version 2.0.14, Panlab; Harvard Apparatus).

One-Trial Novel Object Recognition Task

One-trial object recognition test is based on the innate tendency of rodents to explore novel objects over familiar ones. Testing consisted of three different phases: a habituation phase, a sample phase, and a test phase. Following initial exposure, four additional 10-min daily habituation sessions were introduced for mice to become familiar with the apparatus (50×50×40 cm) and the surrounding environment. On the fifth day, every mouse was first submitted to the sample phase of which two identical objects were placed in a symmetric position from the center of the arena and was allowed to freely explore the objects for 8 min. After a 15-min delay during which the mouse was returned to its home cage, the animal was reintroduced in the arena to perform the test phase. The mouse was then exposed to two objects for another 5 min: a familiar object (previously presented during the sample phase) and a novel object, placed at the same location as during the sample phase. Data collection was performed using a video tracking system (ANY-Maze version 4.5 software; Stoelting Co.). Object discrimination index was evaluated by the index: [(time spent exploring the new object)/(time spent exploring both old and new objects)] during the test phase.

Novel Object Location Test

The object location memory task is used to evaluate hippocampal-dependent spatial memory in rodents through an evaluation of the ability of rodents to explore the new location of a familiar object with respect to spatial cues. This test is based on the spontaneous tendency of rodents to spend more time exploring when a familiar object has been relocated. Testing was conducted in an open field apparatus (50×50×40 cm). The mice were first acclimated to the chamber for ten minutes one day for two days prior to testing. On the third day during the acquisition phase mice were allowed to explore two duplicate objects, which were placed in the far corners of the arena for 8 min. After a delay of 15 min, one object was placed in the corner diagonally opposite. Thus, both objects in the phase were equally familiar, but one was in a new location. The position of the new object was counterbalanced between mice. The objects were cleaned with 70% ethanol after each trial. The time spent exploring each object was measured. A discrimination index was calculated: [(new location object exploring time)/(time spent exploring both familiar and new location objects)×100] during the test phase.

Tissue Processing

All mice were sacrificed by cervical dislocation. Forebrain cortex and hippocampus were detached immediately from the left hemisphere and frozen in dry ice for biochemical analysis. The right hemisphere was fixed in 4% paraformaldehyde in 100 mM phosphate buffered (PB) for at least 24 hours at room temperature. Tissues were then post-fixed in a 30% sucrose solution at 4° C. for overnight and 40 µm sagittal sections of the entire half hemisphere were cut using a freezing microtome. The sections were stored in glycol anti-freeze solution (ethylene glycol, glycerol and 100 mM PBS in 3:3:4 ratio) at −20° C. until further processing.

Western Blot Analysis

Mouse brain tissue was homogenized in pre-chilled buffer containing 50 mM Tris-HCl, (pH 7.4), 100 mM sodium fluoride, and 1 mM sodium othovanadate, 1 mM EDTA, 0.5 mM AEBSF, 10 µg/ml aprotinin, 10 µg/ml leupeptin, 4 µg/ml pepstatin. Each homogenate was boiled in 2× Laemmli's buffer for 5 min and protein concentration was measured by Pierce™ 660 nm protein assay (Thermo Scientific, Rockford, Ill., USA). The samples were resolved in 10% SDS-PAGE and electro-transferred onto Immobilon-P membrane (Millipore, Bedford, Mass., USA). The blots were then probed with primary antibodies (Table 2 above) and developed with the corresponding horseradish peroxidase-conjugated secondary antibodies and ECL kit (Pierce, Rockford, Ill.). Densitometrical quantification of protein bands in Western blots were analyzed by using the Multi Gauge V3.0 software (Fuji Photo Film Co., Ltd).

Immunohistochemical Staining

Immunohistochemical quantification of abnormally hyperphosphorylated tau was performed on 3-4 sections from minimum 4 mice per group. Free-floating sagittal sections were washed in 10 mM PBS (15 min×3) and then incubated in 0.5% Triton X-100 for 20 min. The sections were again washed in 10 mM PBS (15 min×3) and blocked in a solution containing 5% normal goat serum and 0.1% Triton X-100 for 30 min. Sections were then incubated at 4° C. overnight with the mouse monoclonal antibody AT8 (Ser202/Thr 205, 1:500), PHF1 (ser396/ser404), and 43D (tau 6-18). The next day, after washing three times for 15 min with 10 mM PBS, Alexa 488-conjugated goat anti-mouse IgG antibody (1:500, Molecular Probes, Carlsbad, Calif., USA) in 10 mM PBS with 0.05% Tween-20 was used as secondary antibody for 2 hours at room temperature. Sections were subsequently washed, mounted, and cover slipped using Fluorogel mounting medium (Electron Microscopy Sciences, Hatfield, Pa., USA). Only brain regions showing overt positive specific staining, namely the CA1 of the hippocampus and the subiculum, were evaluated. Maximum projection images were generated based on confocal z-stacks using Nikon 90i fluorescent microscope equipped with Nikon C1 three-laser confocal system and a Nikon DS U1 digital camera. The AT8 immunoreactive load was quantified using NIH Image J (v.1.46r).

Human Aβ40 Measurements by ELISA

The tissue from forebrain cortex was homogenized in 10 volumes of ice-cold guanidine hydrochloride buffer (50 mM Tris-HCl, pH 8.0, 5.0 M guanidine.HCl). The homogenate was mixed for 4 hours at room temperature, and then stored at −20° C. For ELISA, each brain homogenate was diluted 1:25 with ice-cold reaction buffer (5% BSA, 0.03% Tween-20, 2.1 mM AEBSF, 20 µg/ml aprotinin, 20 µg/ml leupeptin, 2.0 mM EDTA, pH 7.4] in DPBS (ThermoScientific, prod #28344) and centrifuged at 16,000×g for 20 min at 4° C. The final concentration of AEBSF was 1 mM to prevent proteolysis of the Aβ peptides, and the final concentration of guanidine hydrochloride was 0.1 M. The supernatant was further diluted 1:1(v/v) with standard diluent buffer and assessed using ELISA kit specific for Human Aβ40 and calibrated with synthetic Aβ peptides from Invitrogen (Cat #KHB3482) according to the manufacturer's instructions. The Aβ40 peptide standards were prepared with the same composition of the buffer used for the dilution of the samples.

Statistical Analysis

Data were analyzed using GraphPad Prism version 5.0 (GraphPad Software Inc, La Jolla, Calif., USA) and one-way or two-way ANOVA (as appropriate) followed by a Bonferroni's posthoc test. Further intergroup comparisons were also performed using un-paired two-tailed t-test. All data are presented as means±SEM, and $p<0.05$ was considered statistically significant.

Results

Immunizations with 43D and 77E9 Antibodies Decreased Total Tau in Hippocampus

As described above, passive immunizations with 43D and 77E9 antibodies, once a week for 4 weeks (i.p., 100 µg/mouse), at 14-17 months old 3×Tg-AD mice, reduced total tau and hyperphosphorylated tau at several sites. To investigate the dose-dependent effect of tau immunization, the 12-month-old 3×Tg-AD mice were immunized with mouse IgG, 43D, 77E9, and mixture of 43D and 77E9, once a week for two weeks (i.v., 15 µg/mouse), and then sacrificed 24 hours after second immunization. Immunization with antibody 43D and antibody 77E9 both reduced human transgenic tau (43D) and total tau level as detected with R134d and 92e antibodies in hippocampus, respectively, as seen in FIG. 6. A significant decrease of hyperphosphorylated tau was not observed after two doses of immunizations with 43D and 77E9 antibodies, as seen in FIG. 6. These results indicate that short immunization with normal N-terminal tau 43D and 77E9 antibodies could reduce the levels of total tau but not hyperphosphorylated tau in the brain.

Six Immunizations with 43D Antibody Reduced Both Total and Hyperphosphorylated Taus in Hippocampus 15 months old 3×Tg-AD mice were immunized with mouse IgG and 43D, once weekly for six weeks (i.v., 15 µg/mouse), and sacrificed the mice on the day after the last immunization. Similar to two immunizations, six immunizations decreased both human transgenic tau (tested with 43D) and total tau level (tested with R134d) in the hippocampus. Importantly, six immunizations significantly reduced hyperphosphoryalted tau at ser262/ser356 (12e8 antibody) and ser396/ser404 (PHF1 antibody) sites, and also showed a clear trend to decrease tau hyperphosphorylation at Thr205 site in hippocampus, as seen in FIG. 7. These results indicated that an increased number of doses of immunization with normal N-terminal tau antibodies could decrease tau pathology in the brain.

Figures 8B, 8C, 8D, 8E:
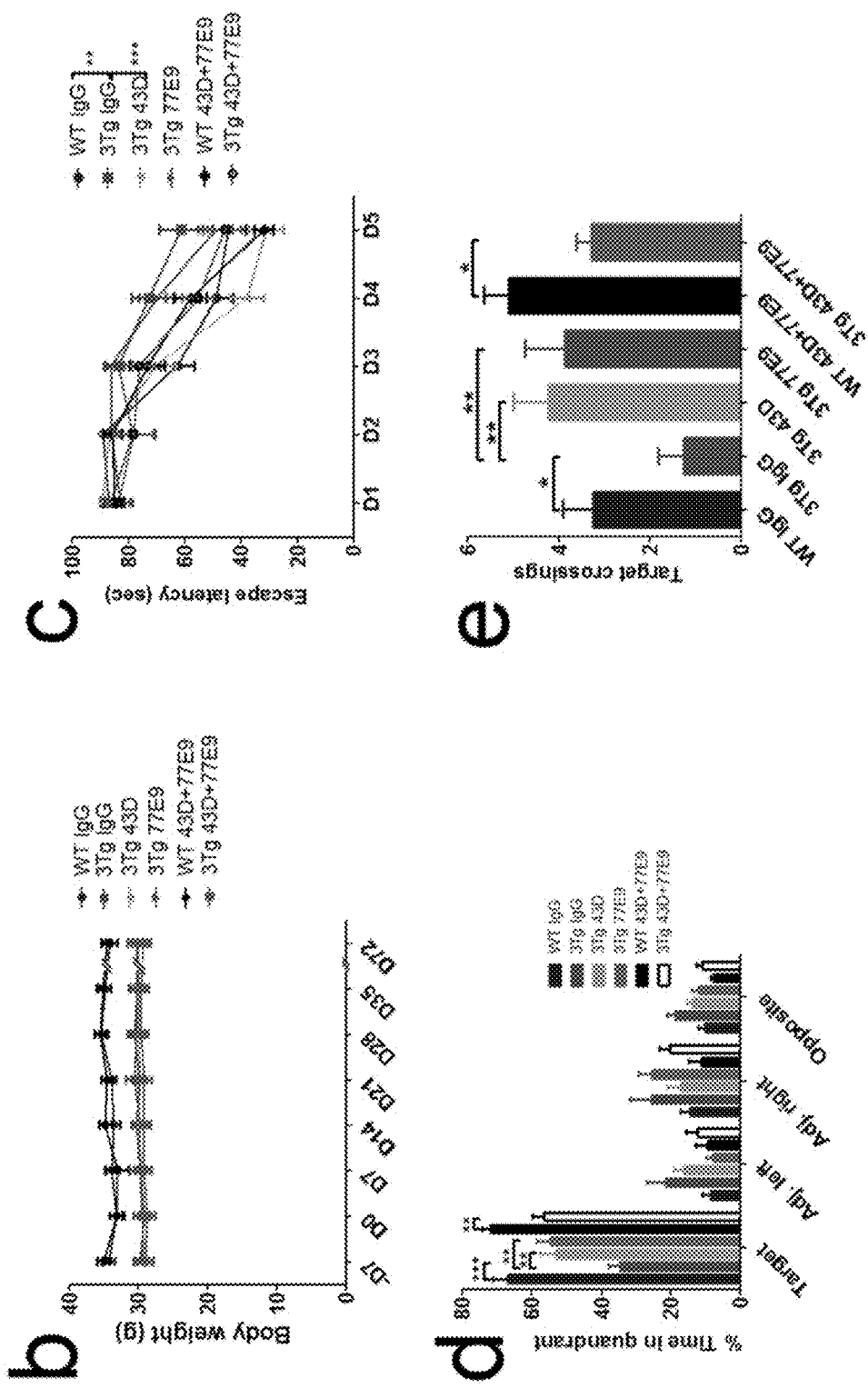
Figures 8F, 8G:
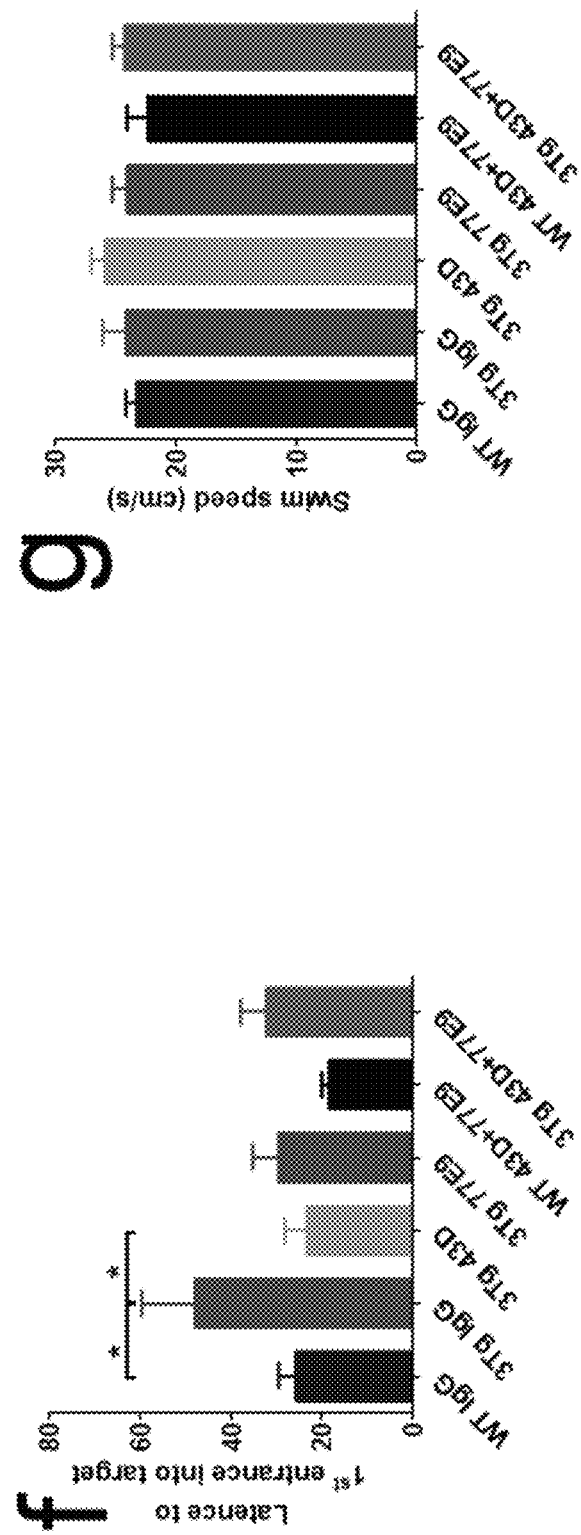

Passive Immunization with 43D and 77E9 Antibodies Rescues Learning and Memory Deficits in 3×Tg-AD Mice To investigate whether passive immunization with normal N-terminal tau antibodies, once weekly for 6 weeks (i.v., 15 µg/mouse), could improve cognitive functions in 3×Tg-AD mice, Morris water maze task was conducted after the 6$^{th}$ injections. 3×Tg-AD mice immunized with 43D antibody took significant less time than the mice treated with mouse IgG to find the hidden platform in acquisition phase, as seen in FIG. 8(c). More importantly, in the probe trial, 3×Tg-AD mice treated with 43D antibody spent longer time, as seen in FIG. 8(d), had more target crossings, as seen in FIG. 8(e), and took much less time to enter the target quadrant, as seen in FIG. 8(f) than that of 3 xTg-AD mice treated with mouse IgG antibody in probe trial. Unlike the mice treated with 43D, 3×Tg-AD mice treated with 77E9 antibody took similar time to that of 3×Tg-AD mice treated mouse IgG to reach the hidden platform in acquisition phase, as seen in FIG. 8(c). However, 3×Tg-AD mice treated with 77E9 antibody performed the similar behavior with that of 3×Tg-AD mice treated with 43D antibody in the probe trial, as seen in FIGS. 8(d) through (f). No significant difference was observed in swim speed during probe trial among all animal groups. Additionally, passive immunization with 43D and 77E9 antibody did not cause significant change in body weight, as seen in FIG. 8(b), and any neurological deficits during the whole period of this study. These results indicated that passive immunization targeting N-terminal tau with 43D and 77E9 antibodies ameliorated the impaired spatial memory without any side effects in 3×Tg-AD mice.

To examine whether passive immunization with tau antibodies could recue the short-term memory impairment in 3×Tg-AD mice, a one-trial object recognition task was conducted with a 15 min interval between the sample phase and the test phase. As compared to WT control mice, 3×Tg-AD mice spent less time exploring the novel object than the familiar object in test phase, as seen in FIG. 9(a). However, 3×Tg-AD mice immunized with 43D and 77E9 spent much longer time exploring the novel object than that of 3×Tg-AD mice treated with mouse IgG, as seen in FIG.

9(b). These results clearly indicated short memory impairment in 3×Tg-AD mice, and a complete rescue of short-term memory deficits by passive immunization with six doses of 43D and 77E9 antibodies in 3×Tg-AD mice.

The Beneficial Effect of Immunization with Tau Antibodies on Improvement of Short-Term Memory Sustained Longer Time Even after Discontinuing Immunization To assess whether the beneficial effect of passive immunization with 43D and 77E9 antibodies could sustain longer time, the novel object location task was used to measure the short memory of mice after 130 days of the last immunization. All the mice spent similar time exploring the objects at location 1 and location 2 in sample phase, as seen in FIG. 10(a). Surprisingly, 3×Tg-AD mice immunized with 43D antibody spent much more time exploring the object in new locations than that of 3×Tg-AD mice treated with mouse IgG in test phase, as seen in FIG. 10(b). 3×Tg-AD mice immunized with 77E9 antibody also showed a clear trend to explore the object at novel locations than that of 3×Tg-AD control mice, as seen in FIG. 10(b). These results indicated that the beneficial effect of passive immunization with 43D and 77E9 antibodies on short-term cognitive improvement could last at least four months after discontinuing immunization.

The Long Term Effect of Passive Immunization with Tau Antibodies 43D and 77E9 on Tau Pathology is Underdetectable by Western Blots in the Forebrain in 3×Tg-AD Mice To assess whether passive immunization with tau antibodies 43D against tau 6-18 and 77E9 against tau 184-195 decreases tau pathology 3×Tg-AD mice, the levels of total and hyperphosphorylated taus were investigated by Western blots in forebrain. No significant difference was observed on total tau level tested with R134d and hyperphosphorylated tau at Ser199, Ser202/Thr205 (AT8), Thr205, Thr231, Ser262/Ser356 (12E8), and Ser396/Ser404 (PHF1) sites in forebrain at five weeks after the sixth immunization, as seen in FIG. 11. Similar results were observed in the forebrain at five months later of sixth immunization (data not shown).

Passive immunization with tau antibodies does not affect Aβ accumulation during moderate to severe stage of plaque pathology.

Figures 7B, 7C, 7D, 7E:
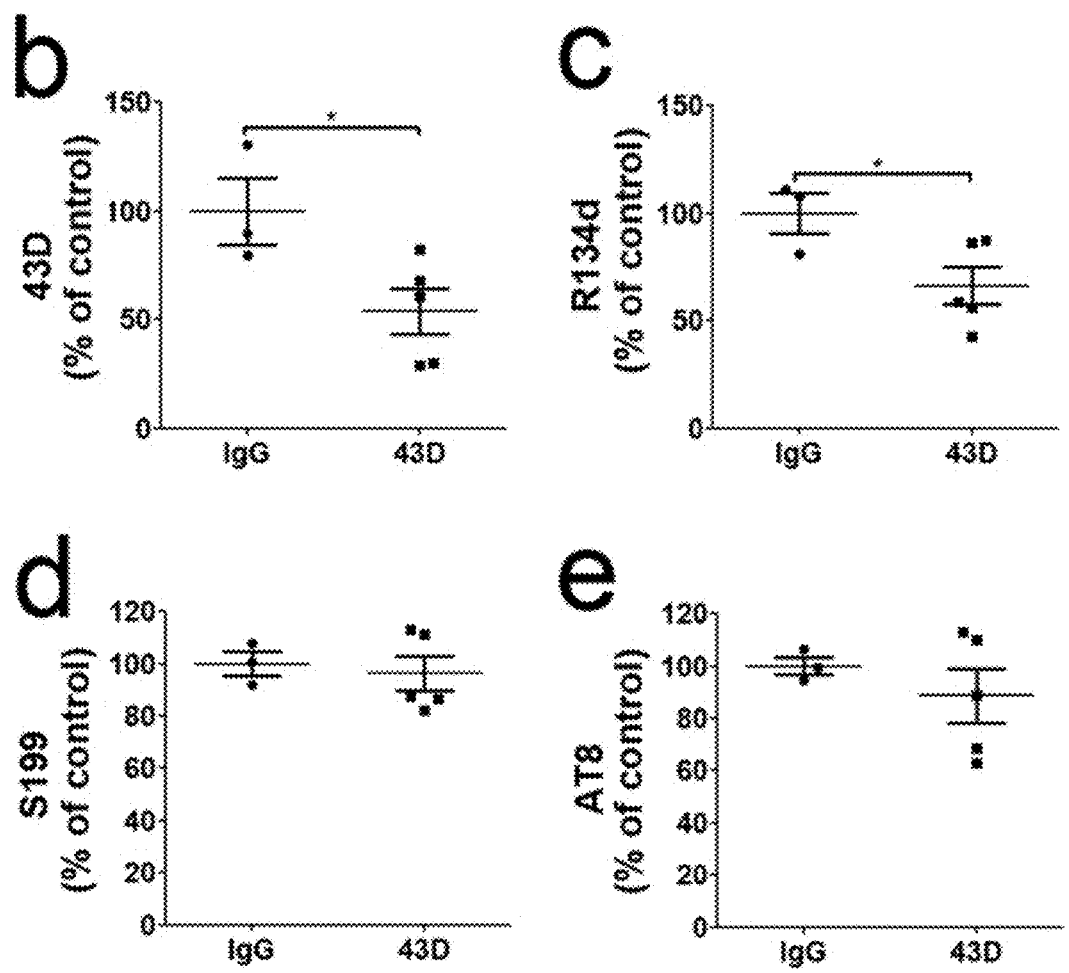
Figures 7F, 7G, 7H:
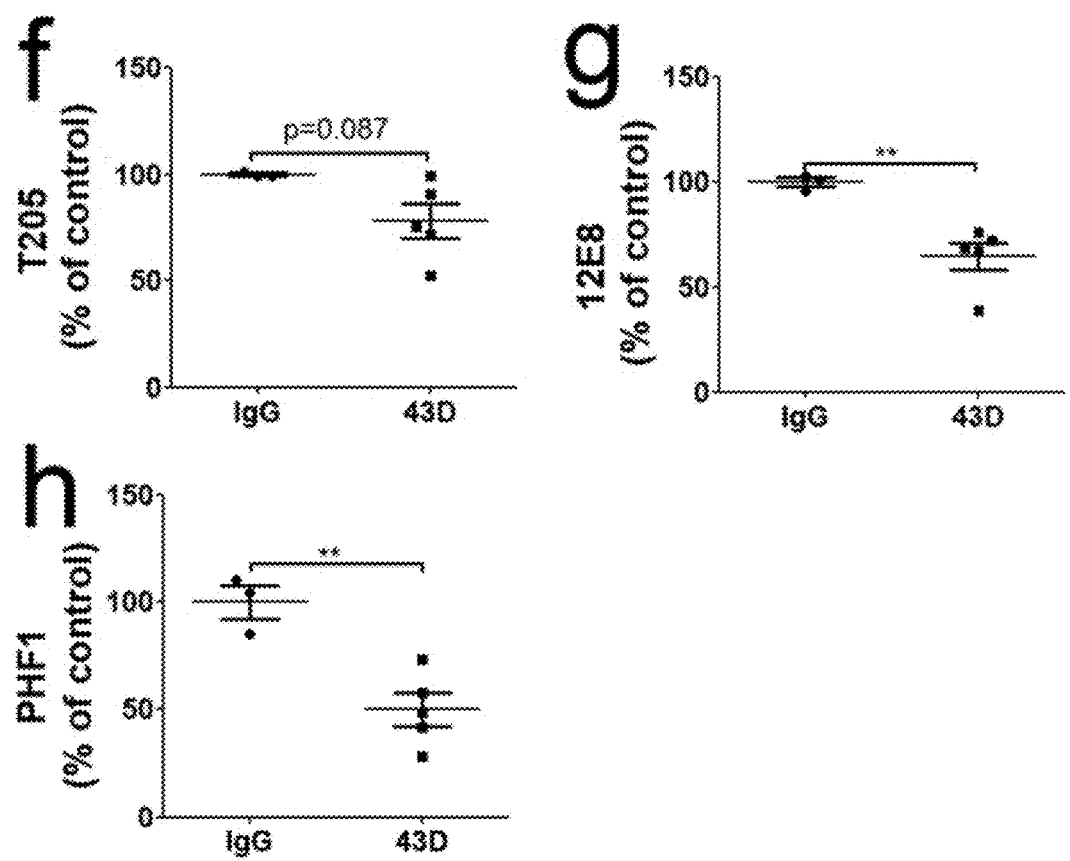
Figures 12A, 12B, 12C:
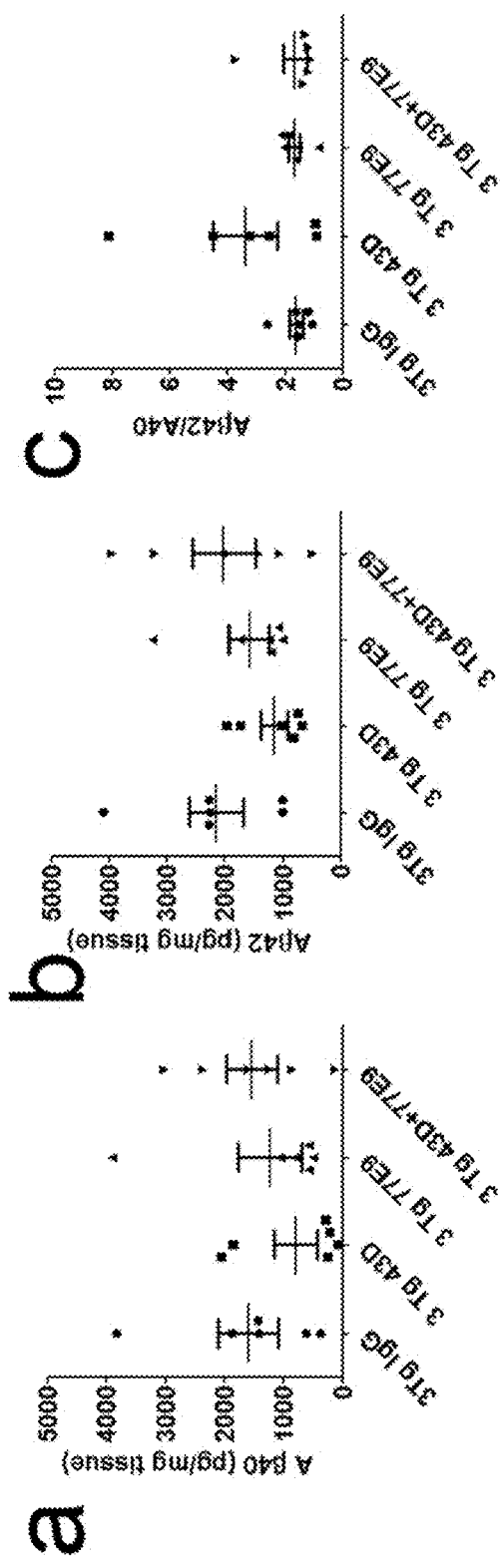
Figures 12D, 12E, 12F:
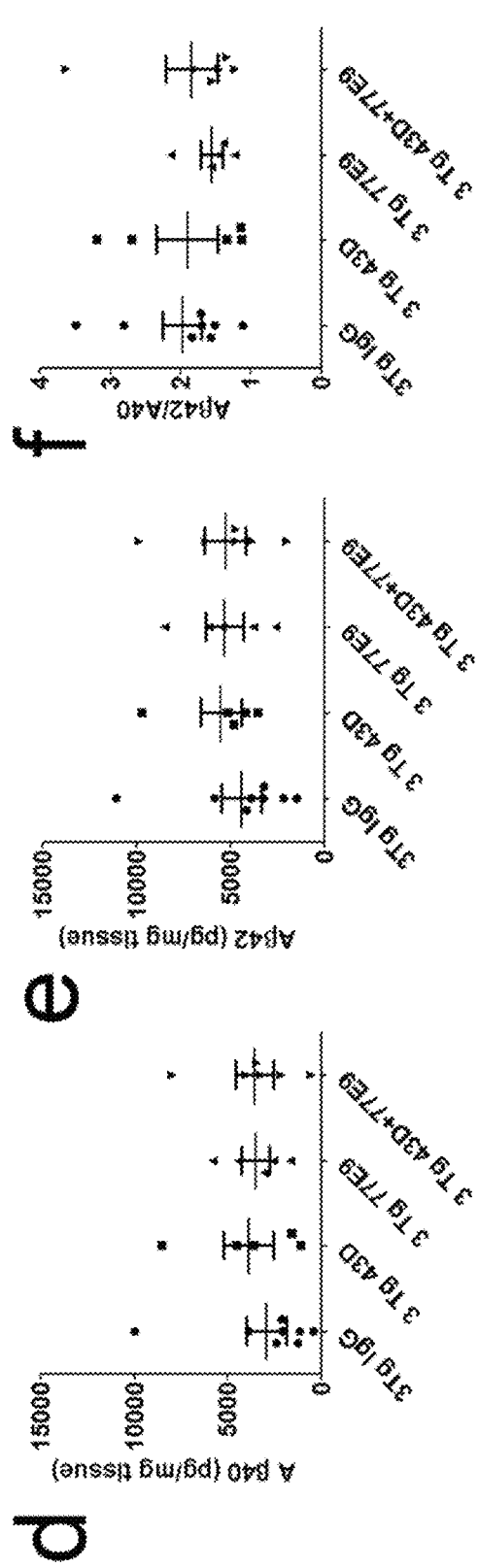

Triple transgenic AD mice develop amyloid plaques starting around nine months of age which is first apparent in the cortex and progresses to the hippocampus with age. In the present examples, it was determined that passive immunization with tau antibodies 43D and 77E9 could alter the level of Aβ. Five weeks after the last immunization with 43D antibody, but not 77E9 antibody, there was a clear trend to decrease the levels of Aβ40 and Aβ42, and increase the ratios of Aβ42/Aβ40 in forebrain, though these changes did not reach significant difference, see FIGS. 12(a) through (c). However, the levels of Aβ40, Aβ42 as well as the ratio of Aβ42/Aβ40 were similar among 43D, 77E9 and mouse IgG immunized 3×Tg-AD mice at five months after the sixth immunization, as seen in FIGS. 12(d) through 7(e). These data suggest that immunotherapy targeting tau 6-18 but not tau 184-195 could reduce the amyloid plaque load in the short term after discontinuing immunizations, with the beneficial effect disappearing in five months without continuing treatment.

In summary, passive immunization targeting N-terminal projection domain of tau 6-18 and 184-195 with 43D and 77E9 antibodies i.v. once weekly for six weeks can rescue spatial memory impairment and short-term memory deficits. Importantly, the beneficial effect of immunization with 43D and 77E9 on short-term memory improvement sustains at least four months after discontinuation of the immunization. Additionally, passive immunization with 43D and 77E9 antibodies has a dose-dependent effect on the reduction of total and hyperphosphorylated tau in hippocampus, though the beneficial effect on tau pathology can be seen in a much shorter time than that in behavioral improvement. The passive immunization targeting N-terminal projection domain of tau had a trend but no statistically significant ameliorating effect on Aβ pathology in the transgenic mice. Overall, the examples of the present invention demonstrate that passive immunization targeting N-terminal projection domain of tau can present a promising treatment opportunity for AD and other tauopathies.

What is claimed is:

1. A method of treating a subject having cognitive impairment associated with a tauopathy, comprising the step of administering a non-naturally occurring monoclonal antibody that binds to tau 6-18 to improve the cognitive impairment of the subject, wherein the monoclonal antibody is a tau antibody 43D.

2. The method of claim 1, wherein the step of administering a non-naturally occurring antibody comprises administering the tau antibody 43D at least twice.

3. The method of claim 2, wherein the step of administering the tau antibody 43D comprises administering the tau antibody 43D once weekly for six weeks.

\* \* \* \* \*